(12) United States Patent
Muranaka et al.

(10) Patent No.: US 12,084,688 B2
(45) Date of Patent: Sep. 10, 2024

(54) GLUCURONOSYLTRANSFERASE, GENE ENCODING SAME AND USE THEREOF

(71) Applicant: RIKEN, Wako (JP)

(72) Inventors: Toshiya Muranaka, Saitama (JP); Hikaru Seki, Saitama (JP); Kazuki Saito, Saitama (JP); Kiyoshi Ohyama, Saitama (JP)

(73) Assignee: RIKEN, Wako (JP)

( * ) Notice: Subject to any disclaimer, the term of this patent is extended or adjusted under 35 U.S.C. 154(b) by 221 days.

(21) Appl. No.: 17/470,085

(22) Filed: Sep. 9, 2021

(65) Prior Publication Data

US 2022/0186195 A1 Jun. 16, 2022

Related U.S. Application Data

(60) Division of application No. 16/234,917, filed on Dec. 28, 2018, now Pat. No. 11,130,945, which is a continuation of application No. 14/782,150, filed as application No. PCT/JP2014/059923 on Apr. 4, 2014, now abandoned.

(30) Foreign Application Priority Data

Apr. 4, 2013 (JP) ................................ 2013-078847

(51) Int. Cl.
| | | |
|---|---|---|
| *C12N 9/10* | (2006.01) | |
| *C12P 19/18* | (2006.01) | |
| *C12P 19/56* | (2006.01) | |
| *C12Q 1/6895* | (2018.01) | |

(52) U.S. Cl.
CPC ............ *C12N 9/1051* (2013.01); *C12P 19/18* (2013.01); *C12P 19/56* (2013.01); *C12Q 1/6895* (2013.01); *C12Y 204/01* (2013.01)

(58) Field of Classification Search
None
See application file for complete search history.

(56) References Cited

U.S. PATENT DOCUMENTS

| 8,969,654 | B2 | 3/2015 | Muranaka et al. |
| 9,193,980 | B2 | 11/2015 | Muranaka |
| 2003/0177518 | A1 | 9/2003 | Osbourn et al. |
| 2004/0002105 | A1 | 1/2004 | Dixon et al. |
| 2011/0173724 | A1 | 7/2011 | Muranaka |
| 2012/0246760 | A1 | 9/2012 | Muranaka et al. |
| 2015/0259653 | A1 | 9/2015 | Muranaka et al. |

FOREIGN PATENT DOCUMENTS

| JP | 2005-137291 | 6/2005 |
| WO | 2003/093425 A2 | 11/2003 |
| WO | 2005/080572 A1 | 9/2005 |
| WO | 2009/020231 A1 | 2/2009 |
| WO | 2010/024437 A1 | 3/2010 |
| WO | 2010/025247 | 3/2010 |
| WO | 2010/025427 | 3/2010 |

OTHER PUBLICATIONS

Melvin R. Gibson, "Glycyrrhiza in Old and New Perspectives," Lloydia-the journal of Natural Products, vol. 41, No. 4, Jul.-Aug. 1978, pp. 348-354.

Koji Kakutani, et al., "Purification of glucuronyl transferase of *Glucyrrhiza glabra* L. and the properties thereof," Journal of the Agricultural Chemical Society of Japan, vol. 75, 2001, 5 pages (with partial English translation).

Lingyong Li, et al., "Genome-wide identification and characterization of putative cytochrome P450 genes in the model legume *Medicago truncatula*," PLANTA, vol. 226, Feb. 2, 2007, pp. 109-123 and cover page.

Takahito Nomura, et al., "Cytochrome P450s in plant steroid hormone synthesis and metabolism," Phytochem Rev., vol. 5, Nov. 15, 2006, pp. 421-432.

Masaaki Shibuya, et al., "Identification of β-amyrin and sophoradiol 24-hydroxylase by expressed sequence tag mining and functional expression assay," The FEBS Journal, vol. 273, 2006, pp. 948-959.

Hikaru Seki, et al., "Licorice β-amyrin 11-oxidase, a cytochrome P450 with a key role in the biosynthesis of the triterpene sweetener glycyrrhizin," PNAS, vol. 105, No. 37, Sep. 16, 2008, pp. 14204-14209.

Hikaru Seki, et al., "Triterpene Functional Genomics in Licorice for Identification of CYP72A154 Involved in the Biosynthesis of Glycyrrhizin," The Plant Cell, vol. 23, No. 11, XP 002677792, Nov. 2011, pp. 4112-4123.

Pimpimon Tansakul, et al., "Dammarenediol-II synthase, the first dedicated enzyme for ginsenoside biosynthesis, in *Panax ginseng*," FEBS Letters, vol. 580, No. 22, XP025232563, Oct. 2, 2006, pp. 5143-5149.

Hiroaki Hayashi, et al., "Cloning and Characterization of a cDNA Encoding β-Amyrin Synthase Involved in Glycyrrhizin and Soyasaponin Biosyntheses in Licorice," Biological & Pharmaceutical Bulletin, vol. 24, No. 8, XP002978733, Aug. 1, 2001, pp. 912-916.

Iddo Friedberg, "Automated protein function prediction—the genomic challenge," Briefings in Bioinformatics, vol. 7, No. 3, 2006, pp. 225-242.

Akira Ikuta, "The Triterpenes from *Stauntonia Hexaphylla* Callus Tissues and their Biosynthetic Significance," Journal of Natural Products, vol. 52, No. 3, 1989, pp. 623-628.

(Continued)

*Primary Examiner* — Medina A Ibrahim

(74) *Attorney, Agent, or Firm* — Oblon, McClelland, Maier & Neustadt, L.L.P.

(57) ABSTRACT

Provided are an enzyme involved in a glycyrrhizin biosynthetic system, a gene of the enzyme and use thereof in order to stably and continuously provide a large amount of glycyrrhizin. Glucuronosyltransferase with an activity of further transferring glucuronic acid to the hydroxy group at the 2-position of glucuronic acid in an oleanane-type triterpenoid monoglucuronide is identified to provide the transferase, a gene for the transferase and use thereof.

15 Claims, 5 Drawing Sheets

Specification includes a Sequence Listing.

(56) References Cited

OTHER PUBLICATIONS

Hideyuki Suzuki, et al., "A genomics approach to the early stages of triterpene saponin biosynthesis in *Medicago truncatula*," The Plant Journal, vol. 32, 2002, pp. 1033-1048.

D. A. H. Taylor, "Triterpenes from *Salvia glutinosa* L.," J. Chem. Soc. (C), 1967, p. 490.

Arifa Ahamed, et al., "An Artificial Sweetener Stimulates the Sweet Taste in Insect: Dual Effects of *Glycyrrhizin* in Phormia regina," Chem. Senses, vol. 26, 2001, pp. 507-515.

International Search Report issued Nov. 24, 2009 in related PCT/JP2009/065197 filed Aug. 31, 2009.

Extended European Search Report issued Jul. 3, 2012 in European Patent Application No. 09810081.1.

Extended European Search Report issued Jan. 20, 2012 in European Patent Application No. 08792426.2.

Japan Office Action issued Sep. 24, 2014 in Japanese Patent Application No. 2010-526810.

International Search Report issued Jun. 3, 2014 in PCT/JP2014/059923 filed Apr. 4, 2014.

Guo et al., 2004, Proceedings of the National Academy of Sciences USA 101: 9205-9210.

Yonekura-Sakakibara and Hanada, 2011, The Plant Journal 66: 182-193.

Extended European Search Report in Application No. 14778418.5-1501, Issued Dec. 9, 2016.

"Medicago truncatula isolate GT99D (iso) flavonoid glycosyltransferase mRNA, complete cds.", Jul. 2, 2007 (Jul. 2, 2007), XP002764767, retrieved from EBI accession No. EM_STD: DQ875465.

Office Action as received in the corresponding Japan Patent Application No. 2015-510149 dated Dec. 12, 2017.

Bio Industry, Satoru Sawai, et al., "Highly Efficient Biosynthesis of Secondary Metabolites of Plants", 2011, Vol. 28, No. 12, p. 6-12 w/English Translation.

Chen et al., 2019, Diversity of O-Glycosyltransferases Contributes to the Biosyntheis of Flavonoid and Tritepenoid Glycosides in Glycyrrhiza uralensis, 2019, ACS Synth. Biol. 16: 1858-1866.

Nagashima et al., 2004, CDNA cloning and expression of isoflavonoid-specific glucosyltransferase from Glycyrrhiza echinata cell-suspension cultures, Planta 218: 456-459.

Keskin, et al., 2004, Protein Science 13: 1043-1055.

Thornton, et al., 2000, Nature Structural Biology, structural genomic supplement, Nov. 2000; 991-994.

Strasser, 2016, Plant protein glycosylation, Glycobiology 26: 926-939.

Yonekura-Sakakibara and Hanada, 2011, An evolutionary view of functional diversity in family 1 glycosyltransferases, The Plant Journal 66: 182-193.

Non-Final Office Action dated Nov. 29, 2019, 3 pages.

Karel Miettinen, et al., "The ancient CYP716 family is a major contributor to the diversification of eudicot triterpenoid biosynthesis", Nature Communications, Article, Received Apr. 22, 2016, Accepted Nov. 24, 2016, Published Feb. 6, 2017, pp. 1-13.

Hikaru Seki, et al., "P450s and UGTs: Key Players in the Structural Diversity of Triterpenoid Saponins", Plant Cell Physiol, 56(8): 1463-1471 (2015).

Kakutani et al., 2001, Purification of glucuronyl transferase of Glycyrrhiza glabra L. and the properties thereof, Journal of the Agricultural Chemical Society of Japan 75, 5 pages, with partial English translation.

Korean Office Action issued on Jan. 21, 2020, in Patent Application No. 10-2015-7031771, 7 pages.

GenBank: ABI94026.1, "(iso)flavonoid glycosyltransferase [Medicago truncatula]", Jul. 2, 2007, 2 pages.

GenBank: DQ875465.1, "Medicago truncatula isolate GT99D (iso)flavonoid glycosyltransferase mRNA, complete cds", Jul. 2, 2007, 2 pages.

A

Glycyrrhetinic acid monoglucuronide
(sugar acceptor substrate, target ion = 647)

Glycyrrhizin (reaction product, target ion = 823)

B

C

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
caccatggac tcctttgggg ttgaaggtga                               30

<210> SEQ ID NO 2
<211> LENGTH: 26
<212> TYPE: DNA
<213> ORGANISM: Artificial
<220> FEATURE:
<223> OTHER INFORMATION: primer

<400> SEQUENCE: 2
ttaagccact gcctccatta atttgt                                   26

<210> SEQ ID NO 3
<211> LENGTH: 7
```

```
<212> TYPE: PRT
<213> ORGANISM: Artificial
<220> FEATURE:
<223> OTHER INFORMATION: consensus sequence of substrate-binding domain
      in glucuronyltransferase
<220> FEATURE:
<221> NAME/KEY: misc_feature
<222> LOCATION: (3)..(3)
<223> OTHER INFORMATION: Xaa is any of amino acids

<400> SEQUENCE: 3

Ser His Xaa Ile Arg Val Val
1               5

<210> SEQ ID NO 4
<211> LENGTH: 506
<212> TYPE: PRT
<213> ORGANISM: Glychyrrhiza uralensis

<400> SEQUENCE: 4

Met Asp Ser Phe Gly Val Glu Gly Asp His Gln Ala Asp Thr Thr Val
1               5                   10                  15

Leu Lys Ala Val Phe Leu Pro Phe Ile Ser Lys Ser His Leu Ile Arg
            20                  25                  30

Val Val Asp Lys Ala Arg Ile Phe Ala Met His Gly Val Asp Val Thr
        35                  40                  45

Ile Ile Thr Thr Pro Ala Asn Ala Ala Phe Gln Thr Ser Ile Asp
50                  55                  60

His Asp Ser Ser Arg Ser Arg Ser Ile Lys Thr His Ile Val Pro Phe
65                  70                  75                  80

Pro Gln Val Pro Gly Leu Pro Gln Gly Phe Glu Arg Leu Asp Ala Asp
                85                  90                  95

Thr Pro Gln His Leu Leu Pro Lys Ile Tyr Gln Gly Leu Ser Ile Leu
            100                 105                 110

Gln Glu Gln Phe Gln Gln Leu Phe Arg Glu Met Arg Pro Asp Phe Ile
        115                 120                 125

Val Thr Asp Met Tyr Tyr Pro Trp Ser Val Asp Ala Ala Ala Glu Leu
130                 135                 140

Gly Ile Pro Arg Leu Val Cys Asn Gly Gly Ser Tyr Phe Ala Gln Ser
145                 150                 155                 160

Ala Val Asn Ser Ile Glu Leu Phe Ser Pro Gln Ala Lys Val Asp Ser
                165                 170                 175

Asn Thr Glu Thr Phe Leu Leu Pro Gly Leu Pro His Glu Val Glu Met
            180                 185                 190

Thr Arg Leu Gln Leu Pro Asp Trp Leu Arg Gly Ala Pro Asn Glu Tyr
        195                 200                 205

Thr Tyr Leu Met Lys Met Ile Lys Asp Ser Glu Arg Lys Ser Tyr Gly
210                 215                 220

Ser Leu Phe Asn Ser Phe Tyr Glu Leu Glu Gly Thr Tyr Glu Glu His
225                 230                 235                 240

Tyr Lys Lys Ala Met Gly Thr Lys Ser Trp Ser Val Gly Pro Val Ser
                245                 250                 255

Leu Trp Val Asn Gln Asp Ala Ser Asp Lys Ala Cys Arg Gly Asp Val
            260                 265                 270

Lys Glu Gly Lys Gly Asp Gly Val Val Leu Thr Trp Leu Asp Ser Lys
        275                 280                 285

Thr Glu Asp Ser Val Leu Tyr Val Ser Phe Gly Ser Met Asn Lys Phe
290                 295                 300
```

```
Pro Lys Thr Gln Leu Val Glu Ile Ala His Ala Leu Glu Asp Ser Gly
305                 310                 315                 320

His Asp Phe Ile Trp Val Val Gly Lys Ile Glu Gly Glu Gly Gly
            325                 330                 335

Ala Asp Phe Leu Arg Glu Phe Gly Lys Lys Val Lys Glu Lys Asn Arg
            340                 345                 350

Gly Tyr Leu Ile Trp Gly Trp Ala Pro Gln Leu Leu Ile Leu Glu His
        355                 360                 365

Pro Ala Val Gly Ala Val Val Thr His Cys Gly Trp Asn Thr Val Met
    370                 375                 380

Glu Ser Val Asn Ala Ser Leu Pro Leu Ala Thr Trp Pro Leu Phe Ala
385                 390                 395                 400

Glu Gln Phe Phe Asn Glu Lys Leu Val Val Asp Val Val Lys Ile Gly
                405                 410                 415

Val Pro Val Gly Val Lys Glu Trp Arg Asn Trp Asn Glu Phe Gly Asp
            420                 425                 430

Glu Val Val Lys Arg Glu Asp Ile Gly Lys Ala Ile Ala Phe Leu Met
            435                 440                 445

Gly Gly Gly Asp Glu Ser Leu Glu Met Arg Lys Arg Val Lys Val Leu
    450                 455                 460

Ser Gly Ala Thr Lys Lys Ala Ile Gln Val Asp Gly Ser Ser Tyr Thr
465                 470                 475                 480

Lys Leu Lys Glu Leu Ile Glu Glu Leu Lys Ser Ile Lys Leu Gln Lys
                485                 490                 495

Val Asn Asn Lys Leu Met Glu Ala Val Ala
            500                 505

<210> SEQ ID NO 5
<211> LENGTH: 1521
<212> TYPE: DNA
<213> ORGANISM: Glychyrrhiza uralensis

<400> SEQUENCE: 5
atggactcct tgggggttga aggtgatcac caagccgaca ccacagtgct gaaggcggtt      60
tttcttccct tcatctcgaa aagtcatctc atccgtgtgg tggacaaagc aaggatcttc    120
gccatgcacg cgtggatgt caccatcatc actacgccgg ccaacgctgc cgcttttccaa    180 acctccattg accacgactc cagccgcagc cgttccatca aaacgcacat cgttccgttc    240
ccccaagtac ccggtctgcc acagggattc gagagactcg atgccgacac tcctcaacac    300
ttgctcccca agatctacca ggggctatcc attctgcaag agcaattcca caactgttc    360 cgtgaaatga ccagatttt catagtcact gacatgtact acccttggag cgtcgatgcc    420
gccgccgagt tgggattcc gaggttggtt tgtaacggtg aagctactt cgctcagtca    480 gctgttaact ccattgagct attttcacca caagccaagg ttgattcaaa taccgagact    540
tttctgcttc ctgggttacc ccatgaggtt gagatgacac gtttgcaact accggattgg    600
cttagaggag caccgaatga gtacacctat tgatgaaga tgatcaagga ttcagagagg    660
aagagttatg ggtcattgtt caatagcttt tatgagcttg aagggactta tgaggagcat    720
tacaagaaag ccatgggaac caagagttgg agtgtggggc cagtttcttt gtgggtgaac    780
caagatgctt ctgataaggc ttgtaggggg gatgttaaag aaggaaaagg agatgggtg    840 gtgcttactt ggctgattc taaaacagag gactctgttt tgtatgtgag ttttgggagc    900
atgaacaagt ccctaaaaac tcagcttgtt gagatagctc atgccctcga agattctggc    960
```

```
catgatttca tttgggtcgt tggcaaaatt gaagaaggtg aaggtggtgc tgattttttg    1020
agggaatttg agaagaaagt gaaagaaaaa aacagaggtt atctgatatg gggttgggca    1080
ccacagcttc tgattctgga gcatcctgcg gttggagcag tggtgactca ttgtgggtgg    1140
aacaccgtta tggaaagtgt gaatgcaagt ttgccattgg caacttggcc attgtttgcg    1200
gagcagttct tcaatgagaa gctagtggtt gatgtggtga agattggtgt gccagttggg    1260
gttaaggaat ggagaaattg gaatgagttt gggatgagg ttgtgaagag gaggacata     1320 ggaaaggcca ttgcttttt gatgggtggt ggagatgagt ccttggaaat gaggaagagg    1380
gtcaaggtgc tcagtggtgc tacaaagaag gctattcagg ttgatgggtc ttcttacacc    1440
aagttgaaag aactcattga ggagctcaag tcaattaagc ttcaaaaggt caacaacaaa    1500
ttaatggagg cagtggctta a                                             1521

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
caccatggag accaccattg atgtggga                                        28

<210> SEQ ID NO 7
<211> LENGTH: 28
<212> TYPE: DNA
<213> ORGANISM: Artificial
<220> FEATURE:
<223> OTHER INFORMATION: primer

<400> SEQUENCE: 7
ctaagctatt ttgtgattga acttttgc                                        28

<210> SEQ ID NO 8
<211> LENGTH: 1497
<212> TYPE: DNA
<213> ORGANISM: Lotus japonicus

<400> SEQUENCE: 8
atggagacca ccattgatgt gggagaagct gaaatgctaa aggcagtttt tcttccattt      60
ccaataacca gtcacaccat tcgtgttgtt gacacggcga ggctcttcgc catgcacggt     120
gtagatgtca ccataatcac cacaccaggc aacaccaaag ttttccaaac ctccattgac     180
cattgtgatt caggccatat tcgaatccat cttgttaact tcccaggaat ccctggtttg     240
ccacaagggt tgaaaccttt cacagctcat actcctcaac atttagtccc tcaaatcttc     300
gagggaattt ccttctgca agacccgatt caacaactct tgctaccat gaaaccagat      360 ttcatcgtct ctgacatgtt cttcccttgg tccgctgatg ctgcagctga gctgggggatt    420 ccacacttga tttatcttgg tggaagctat atctccaggt ctgcacgcaa ctccattgaa    480
caatatgcgc ctcacaccaa ggtggactct gattctgagc cttttctgct tcctgggtta    540 cccacaagc tgcacatgac aagattgcag ttgccggcac aaactagaga acgcaaccat    600
ctcactgagt taatgaagac tgtgaaagaa tctgagaaga gagctacgg ttcactgatc    660 aatagcttct atgaatttga ggggatttac gaggagcatt acaagacaac cacaggaaca    720
aagagttgga gtgttgggcc agtttcattg tgggtgaacc aagatgagtc agataaggat    780
```

```
gttagaggcg gtgccagtga agaacgagaa ccagaagggt ggcttacttg gcttgattca        840
aaaacagagg actctgttct ctatgtgtgt tttgggagca tgaacaagtt cagcacttct        900
cagcttgttg aaatagctca tgcccttgag gattttggcc atgatttcat ctgggtcgtt        960
ggaaaatttg aagatcaagg tgaaattggg ggtgtaaatg gtttcttgaa agaatttgag       1020
aacagagtgg tggtgaaaag cagaggttat ttaattaggg gttgggcacc acaacttctt       1080
atactggatc accctgcgat ggaggtgtg gtgactcact gtgggtggaa cactactctt        1140
gaaagcgtca ttgcagggtt gccaatggca acgatgcctc ttttttgcaga gcagttttac      1200
aatgagaagt tgctggtgga tgtgctggga attggcgtct ctattggagt gaaaaaatgg       1260
aaaaaatgga atgaggttgg ggatgagata gtgaagaggg agaacatagt gaaggcgatt       1320
tctttgttga tgggtggtgg agaagaggct ttagaaatga ggagaagagc aagagtgctt       1380
ggtgaggctg caaagaaaac tatccagcct ggtgggtgtt ctcacaccaa ggtgaaaggg       1440
ttgattgatg agttgaaggc acttaaattg caaaagttca atcacaaaat agcttag          1497

<210> SEQ ID NO 9
<211> LENGTH: 498
<212> TYPE: PRT
<213> ORGANISM: Lotus japonicus

<400> SEQUENCE: 9

Met Glu Thr Thr Ile Asp Val Gly Glu Ala Glu Met Leu Lys Ala Val
1               5                   10                  15

Phe Leu Pro Phe Pro Ile Thr Ser His Thr Ile Arg Val Val Asp Thr
                20                  25                  30

Ala Arg Leu Phe Ala Met His Gly Val Asp Val Thr Ile Ile Thr Thr
            35                  40                  45

Pro Gly Asn Thr Lys Val Phe Gln Thr Ser Ile Asp His Cys Asp Ser
        50                  55                  60

Gly His Ile Arg Ile His Leu Val Asn Phe Pro Gly Ile Pro Gly Leu
65                  70                  75                  80

Pro Gln Gly Phe Glu Thr Phe Thr Ala His Thr Pro Gln His Leu Val
                85                  90                  95

Pro Gln Ile Phe Glu Gly Ile Ser Leu Leu Gln Asp Pro Ile Gln Gln
            100                 105                 110

Leu Phe Ala Thr Met Lys Pro Asp Phe Ile Val Ser Asp Met Phe Phe
        115                 120                 125

Pro Trp Ser Ala Asp Ala Ala Ala Glu Leu Gly Ile Pro His Leu Ile
130                 135                 140

Tyr Leu Gly Gly Ser Tyr Ile Ser Arg Ser Ala Arg Asn Ser Ile Glu
145                 150                 155                 160

Gln Tyr Ala Pro His Thr Lys Val Asp Ser Asp Ser Glu Pro Phe Leu
                165                 170                 175

Leu Pro Gly Leu Pro His Lys Leu His Met Thr Arg Leu Gln Leu Pro
            180                 185                 190

Ala Gln Thr Arg Glu Arg Asn His Leu Thr Glu Leu Met Lys Thr Val
        195                 200                 205

Lys Glu Ser Glu Lys Ser Tyr Gly Ser Leu Ile Asn Ser Phe Tyr
210                 215                 220

Glu Phe Glu Gly Ile Tyr Glu Glu His Tyr Lys Thr Thr Gly Thr
225                 230                 235                 240

Lys Ser Trp Ser Val Gly Pro Val Ser Leu Trp Val Asn Gln Asp Glu
                245                 250                 255
```

-continued

```
Ser Asp Lys Asp Val Arg Gly Gly Ala Ser Glu Glu Arg Glu Pro Glu
            260                 265                 270
Gly Trp Leu Thr Trp Leu Asp Ser Lys Thr Glu Asp Ser Val Leu Tyr
            275                 280                 285
Val Cys Phe Gly Ser Met Asn Lys Phe Ser Thr Ser Gln Leu Val Glu
            290                 295                 300
Ile Ala His Ala Leu Glu Asp Phe Gly His Asp Phe Ile Trp Val Val
305                 310                 315                 320
Gly Lys Phe Glu Asp Gln Gly Glu Ile Gly Gly Val Asn Gly Phe Leu
                325                 330                 335
Lys Glu Phe Glu Asn Arg Val Val Val Lys Ser Arg Gly Tyr Leu Ile
                340                 345                 350
Arg Gly Trp Ala Pro Gln Leu Leu Ile Leu Asp His Pro Ala Ile Gly
            355                 360                 365
Gly Val Val Thr His Cys Gly Trp Asn Thr Thr Leu Glu Ser Val Ile
    370                 375                 380
Ala Gly Leu Pro Met Ala Thr Met Pro Leu Phe Ala Glu Gln Phe Tyr
385                 390                 395                 400
Asn Glu Lys Leu Leu Val Asp Val Leu Gly Ile Gly Val Ser Ile Gly
                405                 410                 415
Val Lys Lys Trp Lys Lys Trp Asn Glu Val Gly Asp Glu Ile Val Lys
            420                 425                 430
Arg Glu Asn Ile Val Lys Ala Ile Ser Leu Leu Met Gly Gly Gly Glu
            435                 440                 445
Glu Ala Leu Glu Met Arg Arg Arg Ala Arg Val Leu Gly Glu Ala Ala
    450                 455                 460
Lys Lys Thr Ile Gln Pro Gly Gly Cys Ser His Thr Lys Val Lys Gly
465                 470                 475                 480
Leu Ile Asp Glu Leu Lys Ala Leu Lys Leu Gln Lys Phe Asn His Lys
                485                 490                 495
Ile Ala
```

GLUCURONOSYLTRANSFERASE, GENE ENCODING SAME AND USE THEREOF

TECHNICAL FIELD

The present invention relates to an enzyme for transferring glucuronic acid to an oleanane-type triterpenoid monoglucuronide, a gene encoding the enzyme and use of the enzyme or the gene.

BACKGROUND ART

A *Glycyrrhiza* plant which is a perennial herbaceous plant is known as an important Chinese herbal medicine (Kampo medicine) and widely used throughout the world. The part of the plant used as a Chinese herbal medicine is principally root and stolon. Metabolite analysis using *G. uralensis*, *G. glabra* and *G. inflata* (Non Patent Literature 1) has clarified that the main active ingredient contained in these parts is glycyrrhizin. Glycyrrhizin is a sweet substance belonging to an oleanane-type triterpenoid saponin. Since glycyrrhizin is useful in view of herbal medicine and pharmacology, various studies have been conducted on glycyrrhizin.

In order to stably and continuously provide high-quality glycyrrhizin serving as a medicinal drug by a biological production system, for example, establishment of optimal production conditions by using a gene involved in a glycyrrhizin biosynthetic system or the expression level of the gene as a marker, selection of a high glycyrrhizin production strain, and breeding of the high glycyrrhizin production plant, introducing a biosynthetic gene is required. Therefore, it is indispensable to identify group of genes involved in the glycyrrhizin biosynthetic system.

It is considered that glycyrrhizin is biologically synthesized from β-amyrin, which is commonly contained in plants, as a precursor substance, through two-stage oxidation reactions and two-stage glycosylation reactions. β-amyrin belongs to an oleanane-type triterpenoid and serves as a precursor substance, from which glycyrrhizin and soyasaponin are biologically synthesized in a triterpenoid saponin biosynthetic system, in short, serves as a branching point for biosynthesis (FIG. 1). The present inventors, up to present, have isolated biosynthetic enzymes involved in the pathway from β-amyrin to glycyrrhizin, more specifically, two types of oxidases, namely, CYP88D6 (Patent Literature 1) and CYP72A154 (Patent Literature 2), which catalyze the two-stage oxidation reactions for biologically synthesizing glycyrrhetinic acid (which is an aglycone of glycyrrhizin) from β-amyrin (FIG. 2). However, genes encoding the enzymes catalyzing two-stage glycosylation reactions to biologically synthesize glycyrrhizin from glycyrrhetinic acid have not yet been found, up to present.

CITATION LIST

Patent Literature

Patent Literature 1: WO2009/020231
Patent Literature 2: WO2010/024437

Non Patent Literature

Non Patent Literature 1: Gibson, M. R., 1978, Lloydia-the journal of Natural Products, 41 (4): 348-354

SUMMARY OF INVENTION

Technical Problem

An object of the present invention is to identify a glycosyltransferase having an activity to transfer a sugar to an oleanane-type triterpenoid in a biosynthetic system of an oleanane-type triterpenoid diglucuronide and a gene encoding the glycosyltransferase in order to stably and continuously provide an oleanane-type triterpenoid diglucuronide including glycyrrhizin in a biological production system, and provide the glycosyltransferase, the gene for the glycosyltransferase and use thereof.

Solution to Problem

The present inventors have conducted intensive studies with a view to solving the aforementioned object. As a result, they successfully isolated, in the biosynthetic system starting from β-amyrin to glycyrrhizin, an enzyme catalyzing the second-stage glycosylation reaction, specifically, a novel glycosyltransferase, which transfers glucuronic acid to an oleanane-type triterpenoid monoglucuronide, and isolated a gene encoding the glycosyltransferase. To describe more specifically, mRNA was prepared from a Fabaceae plant, and thereafter, a cDNA library was prepared and EST analysis was performed. The inventors predicted that glycosyltransferase may be involved in the biosynthetic pathway and screened the cDNA library by use of the nucleotide sequence of a known glycosyltransferase gene to narrow candidate genes. Each of the candidate genes was subjected to gene expression analysis to identify a gene having a desired activity and highly expressed in stolon and root. As a result, the present invention was accomplished. More specifically, the present application provides the following inventions.

(1) A polypeptide having an activity to transfer glucuronic acid to the hydroxy group at the 2-position of glucuronic acid in an oleanane-type triterpenoid monoglucuronide.

(2) The polypeptide according to (1), in which the oleanane-type triterpenoid monoglucuronide is selected from the group consisting of β-amyrin monoglucuronide, 11-oxo-β-amyrin monoglucuronide, 30-hydroxy-11-oxo-β-amyrin monoglucuronide, 30-hydroxy-β-amyrin monoglucuronide, 11-oxoglycyrrhetinic acid monoglucuronide and glycyrrhetinic acid monoglucuronide.

(3) The polypeptide according to (1) or (2), derived from a *Glycyrrhiza* plant or a *Medicago* plant.

(4) The polypeptide according to (3), in which the *Glycyrrhiza* plant is *G. uralensis*.

(5) The polypeptide according to any of (1) to (4), containing an amino acid sequence represented by SEQ ID NO: 3.

(6) The polypeptide according to any of (1) to (4), containing any of amino acid sequences of the following (a) to (c):

(a) an amino acid sequence represented by SEQ ID NO: 4, (b) an amino acid sequence derived from the amino acid sequence represented by SEQ ID NO: 4 by deletion, replacement or addition of one or several amino acids, and (c) an amino acid sequence having 80% or more identity with the amino acid sequence represented by SEQ ID NO: 4.

(7) A polynucleotide encoding the polypeptide according to any of (1) to (6).

(8) The polynucleotide according to (7), containing any of nucleotide sequences of the following (d) to (g).
(d) a nucleotide sequence represented by SEQ ID NO: 5,
(e) a nucleotide sequence derived from the nucleotide sequence represented by SEQ ID NO: 5 by deletion, replacement or addition of one or several nucleotides,
(f) a nucleotide sequence having 80% or more identity with the nucleotide sequence represented by SEQ ID NO: 5 or
(g) a nucleotide sequence capable of hybridizing with a complementary nucleotide sequence to the nucleotide sequence represented by SEQ ID NO: 5 under stringent conditions.
(9) A recombinant vector containing the polynucleotide according to (7) or (8).
(10) The recombinant vector according to (9), which is an over-expression vector or a constitutive expression vector.
(11) A transformant containing the recombinant vector according to (9) or (10) or a progeny thereof.
(12) The transformant or a progeny thereof according to (11), which is a Fabaceae plant.
(13) A method for producing a polypeptide having an activity to transfer glucuronic acid to the hydroxy group at the 2-position of glucuronic acid in an oleanane-type triterpenoid monoglucuronide, comprising the steps of culturing the transformant or progeny thereof according to (11) or (12) and extracting the polypeptide according to any of (1) to (6) from the culture.
(14) A method for producing glycyrrhetinic acid monoglucuronide, comprising the step of suppressing an activity of the polypeptide according to any of (1) to (6) in an individual or cell capable of biologically synthesizing glycyrrhizin from β-amyzin.
(15) The production method according to (14), in which the suppression is to suppress an expression of a gene encoding the polypeptide according to any of (1) to (6) or suppress the polypeptide by a treatment with an activity inhibitor.
(16) A method for selecting a plant having the polynucleotide according to (7) or (8) by detecting the presence or absence of the polynucleotide or expression thereof, comprising subjecting a sample containing a nucleic acid prepared from a target plant to a nucleic acid amplification or nucleic acid hybridization using the polynucleotide or a fragment thereof and detecting or quantifying the polynucleotide.

Note that glycyrrhizin, the biosynthetic pathway from β-amyrin to glycyrrhizin and the intermediate products in the pathway in the specification primarily include 20-epi-glycyrrhizin, which is an isomer at the 20-position of glycyrrhizin, a biosynthetic pathway from β-amyrin to 20-epi-glycyrrhizin, and the intermediate products in the pathway, respectively.

The specification includes the contents described in the specification and/or the drawings of Japanese Patent Application No. 2013-078847 based on which the priority of the present application is claimed.

Advantageous Effects of Invention

According to the present invention, there are provided a polypeptide having an activity to transfer glucuronic acid to the hydroxy group at the 2-position of glucuronic acid in an oleanane-type triterpenoid monoglucuronide, a polynucleotide encoding the polypeptide or use thereof.

BRIEF DESCRIPTION OF DRAWINGS

FIG. 4-B A. shows a conceptual diagram when sample B (negative control) in FIG. 4-A was used. B. shows detection results of glycyrrhetinic acid monoglucuronide before sample B, which is a protein extract obtained from a yeast transformed with an empty vector and expressing no GuUGT73.8, is added to a solution containing a sugar acceptor substrate, i.e., glycyrrhetinic acid monoglucuronide, and a sugar donor substrate, i.e., UDP-glucuronic acid. The peak pointed by an open arrow shows glycyrrhetinic acid monoglucuronide. C. shows the results of LC-MS analysis of a reaction solution to which sample B was added and which was subjected to in vitro enzyme assay.

DESCRIPTION OF EMBODIMENTS

Figure 1:
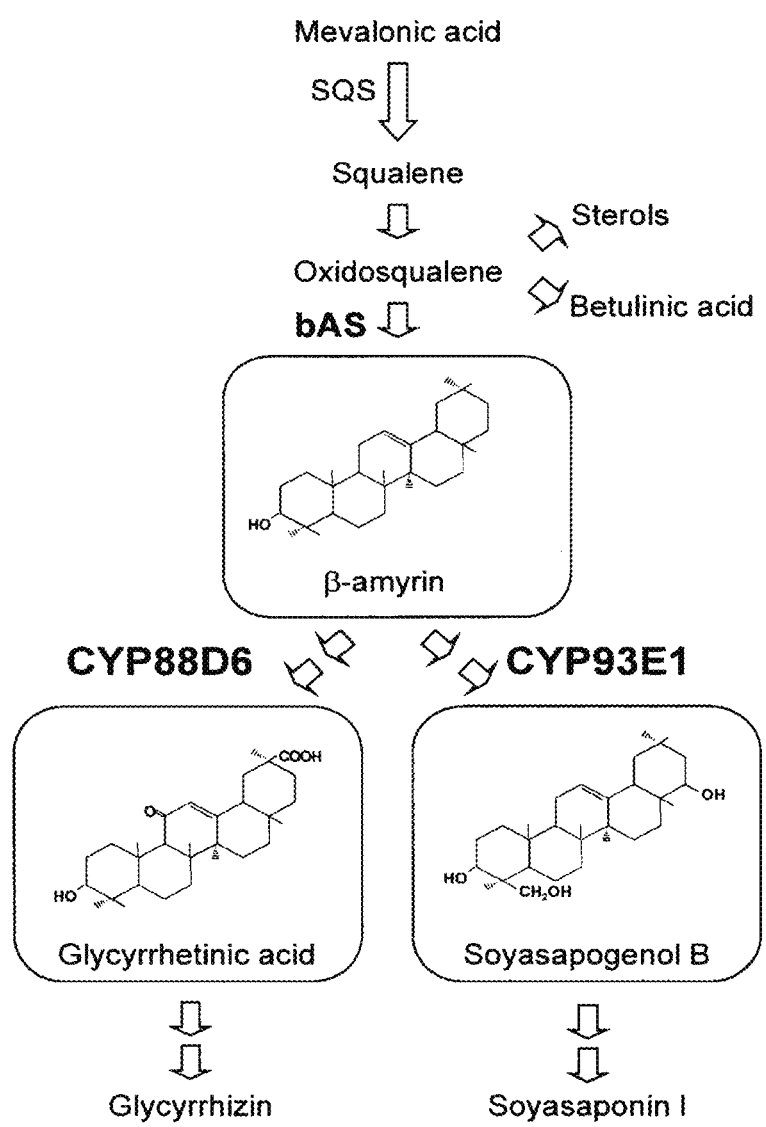
FIG. 1 shows biosynthetic pathways of glycyrrhizin and soyasaponin I in a triterpenoid saponin biosynthetic system.

Now, the present invention will be more specifically described below.

1. Glucuronosyltransferase 2 and Active Fragment Thereof

A first aspect of the present invention relates to a polypeptide having glucuronic acid transfer activity 2.

In the specification, the "glucuronic acid transfer activity 2" refers to the activity to catalyze a second-stage glucuronic acid transfer reaction (glucuronic acid transfer reaction 2) with an oleanane-type triterpenoid which has undergone a first-stage glucuronic acid transfer reaction (glucuronic acid transfer reaction 1), i.e., an oleanane-type triterpenoid monoglucuronide.

In the specification, the "polypeptide having glucuronic acid transfer activity 2" refers to glucuronosyltransferase 2 having an activity to transfer glucuronic acid to an oleanane-type triterpenoid monoglucuronide or an active fragment thereof.

The "oleanane-type triterpenoid" refers to C30 isoprenoid having a pentacyclic oleanane skeleton and comprised of 6 isoprene units. For example, oleanolic acid, hederagenin, β-amyrin, camelliagenin, soyasapogenol, saikogenin, 11-oxo-β-amyrin, 30-hydroxy-β-amyrin, 30-hydroxy-11-oxo-β-amyrin, 11-deoxoglycyrrhetinic acid and glycyrrhetinic acid correspond thereto.

The "oleanane-type triterpenoid monoglucuronide" refers to a compound obtained by transferring a single glucuronic acid to the hydroxy group (OH group) at the 3-position of an oleanane-type triterpenoid. For example, oleanolic acid monoglucuronide, hederagenin monoglucuronide, β-amyrin monoglucuronide, camelliagenin monoglucuronide, soyasapogenol monoglucuronide, saikogenin monoglucuronide, 11-oxo-β-amyrin monoglucuronide, 30-hydroxy-β-amyrin monoglucuronide, 30-hydroxy-11-oxo-β-amyrin monoglucuronide, 11-deoxoglycyrrhetinic acid monoglucuronide and glycyrrhetinic acid monoglucuronide correspond thereto.

In the specification, the "glucuronosyltransferase 2" refers to an enzyme having glucuronic acid transfer activity 2 to transfer a glucuronic acid further to the hydroxy group at the 2-position of glucuronic acid in an oleanane-type triterpenoid monoglucuronide. Owing to the activity, an oleanane-type triterpenoid diglucuronide is produced from an oleanane-type triterpenoid monoglucuronide. Owing to this, glycyrrhizin can be obtained from, for example, glycyrrhetinic acid monoglucuronide. As glucuronosyltransferase 2, for example, a polypeptide containing an amino acid sequence represented by SEQ ID NO: 3 (Ser-His-Xaa-Ile-Arg-Val-Val: Xaa represents any amino acid, preferably Leu or Thr) as a substrate binding site, is mentioned. Alternatively, a polypeptide containing (a) an amino acid sequence represented by SEQ ID NO: 4, (b) an amino acid sequence derived from the amino acid sequence represented by SEQ ID NO: 4 by deletion, replacement or addition of one or several amino acids or (c) an amino acid sequence having 80% or more identity with the amino acid sequence represented by SEQ ID NO: 4, is mentioned.

The "amino acid sequence represented by SEQ ID NO: 4" refers to glucuronosyltransferase 2 (GuUGT73.8) derived from G. uralensis. GuUGT73.8 contains a substrate-binding site consisting of an amino acid sequence represented by SEQ ID NO: 3 in the range from the 28-position to 34-position, provided that the initiation methionine is defined as the 1-position. Furthermore, orthologues of GuUGT73.8 are preferably used as glucuronosyltransferase 2 herein. For example, a Lotus japonicus orthologue of GuUGT73.8 consisting of an amino acid sequence represented by SEQ ID NO: 9 is mentioned. The amino acid sequence represented by SEQ ID NO: 9 has 66.9% identity with the amino acid sequence represented by SEQ ID NO: 4. Furthermore, an amino acid sequence derived from the amino acid sequence represented by SEQ ID NO: 4 by deletion, replacement or addition of one or a plurality of amino acids may be used in the present invention. For example, an amino acid sequence derived from the amino acid sequence represented by SEQ ID NO: 4 by deletion of 1 to 10, preferably 1 to 5, more preferably 1 to 3 or 1 to 2 amino acids; an amino acid sequence derived from the amino acid sequence represented by SEQ ID NO: 4 by addition of 1 to 10, preferably 1 to 5, more preferably 1 to 3 or 1 to 2 amino acids; or an amino acid sequence derived from the amino acid sequence represented by SEQ ID NO: 4 by replacement of 1 to 10, preferably 1 to 5, more preferably 1 to 3 or 1 to 2 amino acids with other amino acids, is mentioned. More specifically, for example, a mutant of glucuronosyltransferase 2 represented by SEQ ID NO: 4 having glucuronic acid transfer activity 2 corresponds thereto.

The "(c) an amino acid sequence having 80% or more identity with the amino acid sequence represented by SEQ ID NO: 4" refers to an amino acid sequence having 80% or more, preferably 85% or more, 90%, 95% or 97% or more amino acid identity with the amino acid sequence represented by SEQ ID NO: 4.

In the present invention, the "active fragment thereof" refers to a polypeptide fragment containing a region of glucuronosyltransferase 2 and having glucuronic acid transfer activity 2. The length of the amino acids of the polypeptide constituting the active fragment is not particularly limited. The region may consist of continuous amino acids of, for example, at least 10, 15, 20, 25, 30, 50, 100 or 150 in (a) to (c) polypeptides.

As the substrate for the polypeptide having glucuronic acid transfer activity 2 of the present invention, an oleanane-type triterpenoid monoglucuronide as mentioned above, preferably, an oleanane-type triterpenoid monoglucuronide involved in the biosynthetic pathway from β-amyrin to glycyrrhizin, is mentioned. More specifically, β-amyrin monoglucuronide, 11-oxo-β-amyrin monoglucuronide, 30-hydroxy-11-oxo-β-amyrin monoglucuronide, 30-hydroxy-β-amyrin monoglucuronide, 11-oxoglycyrrhetinic acid monoglucuronide or glycyrrhetinic acid monoglucuronide is mentioned.

The organism species from which the polypeptide of the present invention is derived, is not particularly limited and preferably a Fabaceae plant. Examples thereof include an Arachis plant, a Cicer plant, an Aspalathus plant, a Dalbergia plant, a Pterocarpus plant, a Desmodium plant, a Lespedeza plant, an Uraria plant, a Galegeae plant, an Astragalus plant, a Glycyrrhiza plant, an Oxytropis plant, an Augyrocytisus plant, a Cytisus plant, a Genista plant, a Spartium plant, a Hedysarum plant, a Cyamopsis plant, an Indigofera plant, a Lotus plant, a Lupinus plant, a Wisteria plant, a Cajanus plant, a Canavalia plant, an Erythrina plant, a Glycine plant, a Hardenbergia plant, a Lablab plant, a Mucuna plant, a Phaseolus plant, a Psophocarpus plant, a Pueraria plant, a Vigna plant, a Robinia plant, a Castanospermum plant, a Maackia plant, an Ormosia plant, a Sophora plant, a Styphnolobium plant, a Medicago plant, a Trigonella plant, a Trifolium plant, a Lathyrus plant, a Lens plant, a Pisum plant and a Vicia plant. Preferably, a Glycyrrhiza plant or a Medicago plant is mentioned. More specifically, e.g., G. uralensis, G. glabra, G. inflata, G. aspera, G. eurycarpa, G. pallidiflora, G. yunnanensis, G. lepidota, G. echinata, G. acanthocarpa or M. truncatula is mentioned.

The polypeptide of the present invention can be extracted by use of a known method. In the case where the polypeptide of the invention is extracted from cultured plant cells, for example, see the method of Hayashi et al. (Hayashi et al., 1996, Phytochemistry, 42: 665-666) for extracting a glucuronosyltransferase from cultured cells of a Glycyrrhiza plant. In the case where the polypeptide of the invention is extracted from an organ or a tissue (e.g., root or stolon) of a plant, see, for example, the method of Noguchi et al. (Noguchi et al., 2007, J. Biol. Chem., 282: 23581-23590) for extracting and purifying a isoflavone glycosidase from soybean. Furthermore, a polypeptide having the amino acid sequence represented by SEQ ID NO: 4 or 9 may be synthesized by a known chemical synthesis method or biologically synthesized by obtaining a gene (described later) encoding the polypeptide with the help of known gene recombination technology and a protein expression system. As to a specific manner for this, see the method described in Green & Sambrook, Molecular Cloning, 2012, Fourth Ed., Cold Spring Harbor Laboratory Press.

The amino acid sequence derived from the amino acid sequence represented by SEQ ID NO: 4 by deletion, replacement or addition of one, several or a plurality of amino acids or the amino acid sequence having 80% or more identity with the amino acid sequence represented by SEQ ID NO: 4, can be obtained, for example, by modifying the polynucleotide described in a second aspect (described later) by a method known in the art. A mutation may be introduced into a gene by a known method such as the Kunkel method or Gapped duplex method or an equivalent method thereto. A mutation can be introduced by e.g., a commercially available mutation introducing kit (for example, Mutant-K (TaKaRa) and Mutant-G (TaKaRa)) using a site-specific mutagenesis method, or an LA PCR in vitro Mutagenesis series kit (TaKaRa). Alternatively, a method of bringing a gene into contact with a mutagenesis agent (for example, an alkylation agent such as ethyl methanesulfonate (EMS), N-methyl-N'-nitro-N-nitrosoguanidine (MNNG)) or a UV irradiation method may be used.

According to the polypeptide of the present invention, an oleanane-type triterpenoid diglucuronide can be obtained by glucuronic acid transfer activity 2 using an oleanane-type triterpenoid monoglucuronide as a sugar acceptor substrate. Furthermore, a method for transferring glucuronic acid to an oleanane-type triterpenoid monoglucuronide by using the polypeptide of the invention can be provided. Accordingly, the polypeptide of the invention and a method for transferring glucuronic acid, if used, enable further elucidation on the glycyrrhizin biosynthetic pathway and synthesis of glycyrrhizin.

2. Polynucleotide Encoding Glucuronosyltransferase 2 and Active Fragment Thereof A second aspect of the present invention relates to a polynucleotide encoding the polypeptide described in the first aspect, more specifically, a polynucleotide encoding glucuronosyltransferase 2 and an active fragment thereof.

The nucleotide sequence of the polynucleotide of the present invention is not particularly limited as long as the polynucleotide encodes the polypeptide of the first aspect having glucuronic acid transfer activity 2. The polynucleotide of the invention is preferably a polynucleotide encoding a polypeptide containing a nucleotide sequence encoding the amino acid sequence represented by SEQ ID NO: 3; a polypeptide containing any one of amino acid sequences described in (a) to (c) in the first aspect; or an active fragment thereof. As a specific example of the polynucleotide, a polynucleotide containing (d) a nucleotide sequence represented by SEQ ID NO: 5, (e) a nucleotide sequence derived from the nucleotide sequence represented by SEQ ID NO: 5 by deletion, replacement or addition of one or several nucleotides, (f) a nucleotide sequence having 80% or more identity with the nucleotide sequence represented by SEQ ID NO: 5 or (g) a nucleotide sequence capable of hybridizing with a complementary nucleotide sequence to the nucleotide sequence represented by SEQ ID NO: 5 under stringent conditions, is mentioned. The polynucleotide having the nucleotide sequence represented by SEQ ID NO: 5 encodes glucuronosyltransferase 2, i.e., GuUGT73.8, derived from G. uralensis. A gene encoding an orthologue of GuUGT73.8 is also preferable as the polynucleotide according to the present aspect. For example, a polynucleotide having a nucleotide sequence represented by SEQ ID NO: 8, which encodes a polypeptide having the amino acid sequence represented by SEQ ID NO: 9, i.e., an orthologue of GuUGT73.8 from L. japonicus, is mentioned. Furthermore, a nucleotide sequence derived from the nucleotide sequence represented by SEQ ID NO: 5 by deletion, replacement or addition of one or a plurality of nucleotides may be used in the present invention. For example, a nucleotide sequence prepared by deleting 1 to 15, preferably 1 to 9, more preferably 1 to 6, 1 to 3 or 1 to 2 nucleotides from the nucleotide sequence represented by SEQ ID NO: 5, a nucleotide sequence prepared by adding 1 to 15, preferably 1 to 9, more preferably 1 to 6, 1 to 3 or 1 to 2 nucleotides to the nucleotide sequence represented by SEQ ID NO: 5, or a nucleotide sequence prepared by replacing 1 to 10, preferably 1 to 5, more preferably 1 to 3 or 1 to 2 nucleotides of the nucleotide sequence represented by SEQ ID NO: 5 with other nucleotides is mentioned.

As the "(f) a nucleotide sequence having 80% or more identity with the nucleotide sequence represented by SEQ ID NO: 5", a nucleotide sequence having 85% or more, 90% or more, 95% or more, or 97% or more identity with the nucleotide sequence represented by the SEQ ID NO: 5 is preferable.

The "(g) stringent conditions" refer to the conditions in which a specific hybrid is formed by base pairing between nucleic acid molecules but a non-specific hybrid is not substantially formed, more specifically, refer to the conditions in which a hybrid can be formed by base pairing between nucleic acid molecules having a high nucleotide-sequence identity (for example, 80% or more, 90% or more, 95% or more or 97% or more) but a hybrid is not substantially formed between nucleic acid molecules except those mentioned above; for example, refer to the conditions in which the temperature of a hybridization reaction falls within the range of 25 to 70° C., preferably 50 to 70° C., more preferably 55 to 68° C.; and/or the concentration of formamide in a hybridization solution falls within the range of 0 to 50%, preferably 20 to 50%, more preferably 35 to 45%. Note that a sodium salt concentration in washing a filter after hybridization is 15 to 750 mM, preferably 15 to 500 mM and more preferably 15 to 300 mM, 15 to 200 mM or 15 to 100 mM.

The polynucleotide of the present invention may further have a nucleotide sequence corresponding to an mRNA precursor containing an intron(s). This is because the nucleotide sequence corresponding to the mRNA precursor comes to be substantially the same sequence as that of the polynucleotide of the invention by a splicing reaction of pre-mRNA; and because the polypeptide encoded by the nucleotide sequence corresponding to the mRNA precursor may have substantially the same function as that of the polypeptide described in the first aspect. For example, a polynucleotide, which has a nucleotide sequence present on the G. uralensis genome and a nucleotide sequence which becomes equivalent to the nucleotide sequence represented by SEQ ID NO: 5 after splicing (i.e., matured mRNA), corresponds thereto. Alternatively, a polynucleotide, which has a nucleotide sequence present on the L. japonicus genome and a nucleotide sequence which becomes equivalent to the nucleotide sequence represented by SEQ ID NO: 8 after splicing (i.e., matured mRNA), corresponds thereto.

The "polynucleotide encoding an active fragment of glucuronosyltransferase 2" refers to a polynucleotide encoding a peptide having glucuronic acid transfer activity 2, which contains a region of continuous nucleotides of at least 10, 15, 20, 25, 30, 50, 100 or 150 in a polynucleotide encoding a polypeptide containing any one of amino acid sequences (a) to (c) of the first aspect, or a polynucleotide having any one of the nucleotide sequences (d) to (g).

The polynucleotide of the present invention may be isolated from an appropriate plant, for example, a Fabaceae plant, preferably, a Glycyrrhiza plant or a Medicago plant, by a known method; and can be obtained for example, by a nucleic acid amplification reaction such as PCR, which is carried out by using a pair of primers (for example, a pair of primers represented by SEQ ID NOs: 1 and 2), each of which has a nucleotide sequence of an appropriate length and is designed based on the nucleotide sequence represented by SEQ ID NO: 5, and using a nucleic acid derived from cDNA library or genomic DNA library of a Glycyrrhiza plant such as G. uralensis, as a template. The polynucleotide of the invention can be also obtained by hybridization using e.g., the aforementioned library as a template and a nucleic acid fragment having a part of the nucleotide sequence represented by SEQ ID NO: 5 as a probe. As to these methods, see the methods described in Green & Sambrook, Molecular Cloning, 2012, Fourth Ed., Cold Spring Harbor Laboratory Press. Alternatively, the polynucleotide of the invention can be synthesized by a known nucleic acid sequence synthesis method such as a chemical synthesis method based on a known nucleotide sequence such as the nucleotide sequence represented by SEQ ID NO: 5.

A nucleotide sequence derived from the nucleotide sequence represented by SEQ ID NO: 5 by deletion, replacement or addition of one, several or a plurality of nucleotides or a nucleotide sequence having 80% or more, preferably 85% or more, 90% or more, 95% or more or 97% or more identity with the nucleotide sequence represented by SEQ ID NO: 5 can be obtained by e.g., introducing a mutation by the method described in the first aspect.

According to the polynucleotide of the present invention, if the polynucleotide of the invention is directly introduced into, or integrated into a recombinant vector of the following third aspect and introduced into various organism species or cells, and allowed to highly express it, glucuronic acid can be transferred to an oleanane-type triterpenoid monoglucuronide.

3. Recombinant Vector

A third aspect of the present invention relates to a recombinant vector containing the polynucleotide described in the second aspect.

The recombinant vector of the present invention can be constructed by introducing the polynucleotide described in the second aspect into an appropriate vector. The type of vector is not particularly limited and may appropriately be selected depending upon the purpose such as cloning or gene expression, or depending upon the host to be introduced (for example, *Escherichia coil,* yeast, an insect cell, an animal cell, a plant cell or a plant body, particularly a *Fabaceae* plant cell or body). An over-expression vector or a constitutive expression vector is particularly preferable. Specific examples of the vector that can be used include, but not particularly limited to, plasmid vectors such as pBI series, pPZP series, pSMA series, pUC series, pBR series, pBluescript series (stratagene) or pTriEX™ series (TaKaRa); viral vectors such as a cauliflower mosaic virus (CaMV), kidney beans mosaic virus (BGMV) or cigarette mosaic viruses (TMV); or binary vectors such as pBI series.

As a method for inserting a desired polynucleotide into a vector as mentioned above, a method known in the art can be used. In a method usually employed, the polynucleotide described in the second aspect is purified, digested with an appropriate restriction enzyme(s), inserted in a corresponding restriction enzyme site or multicloning site of an appropriate vector as mentioned above and ligated thereto. As to a specific manner, see, for example, Green & Sambrook, Molecular Cloning, 2012, Fourth Ed., Cold Spring Harbor Laboratory Press.

The recombinant vector of the present invention may contain, other than a desired polynucleotide described in the second aspect, for example, a regulatory region such as a promoter, an enhancer or a terminator, or a selecting marker gene and/or other genes.

The type of promoter, enhancer, terminator or selecting marker is not particularly limited and may be appropriately selected depending upon the purpose or the host to be introduced as is the case with the vector.

As a workable promoter in plant cells, e.g., a cauliflower mosaic virus (CaMV)35S promoter, a promoter of a nopaline synthase gene (Pnos), a corn-derived ubiquitin promoter, a rice plant-derived actin promoter or a tobacco-derived PR protein promoter is mentioned. As a workable promoter in bacterial cells, e.g., a promotor of a maltogenic amylase gene of *Bacillus stearothermophilus,* α-amylase gene of *Bacillus licheniformis,* a BAN amylase gene of *Bacillus amyloliquefaciens,* an alkaliprotease gene of *Bacillus subtillis* or a xylosidase gene of *Bacillus pumilus;* a PR or PL promoter of phage lambda; or lac, trp or tac promoter of *E. coli* is mentioned. As a workable promoter in yeast host cells, e.g., a promoter derived from a yeast glycolytic gene, an alcohol dehydrogenase gene promoter, a TPI1 promoter or an ADH2-4c promoter is mentioned. As a workable promoter in fungus, an ADH3 promoter or a tpiA promoter is mentioned. As a workable promoter in animal cells, an SV40 early promoter, an SV40 late promotor or a CMV promoter is mentioned. As a workable promoter in insect cells, a polyhedrin promoter, a P10 promoter, a basic protein promoter of a baculovirus, i.e., *Autographa californica polyhedrosis,* a baculovirus immediate early gene 1 promoter or a baculovirus 39K delayed early gene promoter is mentioned.

As an enhancer, e.g., an enhancer region including an upstream sequence within the CaMV 35S promoter, SV40 enhancer or CMV enhancer is mentioned.

As a terminator, a terminator of a nopaline synthase (NOS) gene, a terminator of an octopine synthase (OCS) gene, a CaMV 35S terminator, a 3' terminator of *E. coli* lipopolyprotein 1pp, a trp operon terminator, an amyB terminator or a terminator of an ADH1 gene is mentioned.

As a selecting marker gene, a drug resistant gene (for example, a tetracycline resistant gene, an ampicillin resistant gene, a kanamycin resistant gene, a hygromycin resistant gene, a spectinomycin-resistant gene, a chloramphenicol resistant gene or a neomycin resistant gene); a fluorescent or luminescent reporter gene (for example, luciferase, β-galactosidase, β-glucuronidase (GUS) or green fluorescent protein (GFP)); or an enzyme gene such as a neomycin phosphotransferase II (NPT II) gene or a dihydrofolate reductase gene is mentioned.

According to the recombinant vector of the present invention, e.g., the operation and/or expression of the polynucleotide described in the second aspect can be easily controlled.

4. Transformant or Progeny Thereof

A fourth aspect of the present invention relates to a transformant or a progeny thereof.

In the specification, the "transformant" refers to a host transformed by introducing the polynucleotide described in the second aspect or the recombinant vector described in the third aspect.

The host to be transformed is not particularly limited as long as it can express the polynucleotide described in the second aspect or the recombinant vector described in the third aspect to be introduced. For example, bacteria such as *E. coli* or *Bacillus subtilis;* yeast such as a budding yeast (*Saccharomyces cerevisiae*), a fission yeast (*Schizosaccharomyces pombe*) or methanol utilizing yeast (*Pichia pastoris*); fungus such as *Aspergillus, Neurospora, Fuzarium* or *Trichoderma;* a monocotyledonous plant such as a Gramineae plant or *dicotyledonous* plant such as *Fabaceae* plant or *Brassicaceae* plant; or a plant cell, an animal cell or an insect cell (for example, sf9 or sf21) is mentioned. When a host is a plant, a *Fabaceae* plant is preferable and a *Glycyrrhiza* plant, a *Medicago* plant or a *Glycine* plant is more preferable. *G. uralensis, M. truncatula* or soybean (*Glycine* max) is particularly preferable.

The transformant of the present invention includes a clone having the same genetic information. For example, if a host is a single cell microbe, which asexually reproduces, such as *E. coli* and yeast, a newly produced clone from a first-generation transformant by e.g., fissuration or budding, is also included in the transformant of the invention. If a host is a plant, a part of a plant body taken from a first-generation transformant, for example, a plant tissue such as epidermis, phloem, parenchyma, xylem or fibrovascular bundle, a plant organ such as a leaf, a petal, a stem, a root or a seed; a clone obtained from a plant cell by plant tissue culture, cuttage, grafting or layering; or a newly produced clone by asexual reproduction from a vegetative reproduction organ, which is obtained from a first-generation transformant, such as rhizome, tuberous root, corm or runner, is also included in the transformant of the invention.

The transformant of the present invention may further have one or more other polynucleotides or recombinant vectors, in addition to the polynucleotide described in the second aspect or a recombinant vector described in the third aspect. The other polynucleotides herein refer to polynucleotides except the polynucleotide described in the second aspect. For example, β-amyrin synthase gene, CYP88D6 or CYP72A154 or any one of the oleanane-type triterpenoid monoglucuronide synthase genes corresponds thereto. The other recombinant vectors refer to recombinant vectors except the recombinant vector described in the third aspect.

The transformant of the present invention can be prepared by introducing a polynucleotide or recombinant vector as mentioned above into an appropriate host.

As a method for introducing a polynucleotide or recombinant vector as mentioned above, a method known in the art such as an agrobacterium method, a PEG-calcium phosphate method, an electroporation method, a liposomal method, a particle-gun method or a microinjection method can be used. The polynucleotide introduced may be integrated into the genomic DNA of a host or may be present while keeping the state of the polynucleotide (for example, still present in a foreign vector) just introduced. Furthermore, the polynucleotide introduced may be continuously maintained in a host cell like a case where the polynucleotide is integrated into the genomic DNA of a host or may be temporarily retained.

After the polynucleotide described in the second aspect or the recombinant vector described in the third aspect is introduced into a host by the aforementioned method, whether the desired polynucleotide is introduced or not can be checked by e.g., a PCR method, a Southern hybridization method, a Northern hybridization method or an in-situ hybridization.

In the specification, the "progeny thereof" is a progeny obtained by sexual reproduction of a first-generation transformant and refers to a host having the polynucleotide described in the second aspect or a recombinant vector described in the third aspect of the present invention in an expressible state. For example, if the transformant is a plant, a seedling of the transformant corresponds thereto. The generation of the progeny is not a matter.

According to the transformant of the present aspect, an oleanane-type triterpenoid monoglucuronide present in a host cell can be efficiently converted into an oleanane-type triterpenoid diglucuronide by enhancing the expression of the polynucleotide introduced. In this manner, a transformant enhanced in production of an intermediate product or a final product in the biosynthetic pathway from β-amyrin to glycyrrhizin can be provided.

Furthermore, a transformant enhanced in expression of the polynucleotide obtained by introducing the polynucleotide described in the second aspect or the recombinant vector described in the third aspect in an expressible state can be provided.

5. Method for Producing Glucuronosyltransferase 2 and Active Fragment Thereof

A fifth aspect of the present invention relates to a method for producing glucuronosyltransferase 2 and an active fragment thereof, the method comprising culturing, transformant of the fourth aspect or a progeny thereof and extracting a polypeptide having glucuronic acid transfer activity 2 described in the first aspect from a culture thereof.

In the present aspect, when the polypeptide described in the first aspect is produced by culturing a transformant or a progeny thereof, it is preferable to use a transformant that can over-express or constitutively express the polynucleotide described in the second aspect or a progeny thereof. For example, in the case of a transformant having the recombinant vector described in the third aspect or a progeny thereof, the vector to be used as the recombinant vector may be an expression vector capable of expressing the polynucleotide described in the second aspect and included therein, constitutively, excessively or in a large amount by induction of expression.

As a medium for culturing a transformant or a progeny thereof, a medium suitable for culturing a host may be used. As the medium, a medium known in the art can be used. Although the medium is not limited, if culture is made by using bacteria such as *E. coli* as a host, for example, LB medium or M9 medium is mentioned. If culture is made by using a yeast as a host, YPD medium, YPG medium, YPM medium, YPDM medium or SMM medium, is mentioned. If culture is made by using a plant as a host, an appropriate culture soil or a hydroponic culture medium is mentioned.

The medium may appropriately contain, for example, a carbon source (e.g., glucose, glycerin, mannitol, fructose, lactose), a nitrogen source (e.g., an inorganic nitrogen source such as ammonium sulfate, ammonium chloride; an organic nitrogen source such as a casein digest, a yeast extract, polypeptone, BACTO tryptone, a beef extract), an inorganic salt (e.g., sodium diphosphate, potassium diphosphate, magnesium chloride, magnesium sulfate, calcium chloride), a vitamin (e.g., vitamin B1), and a drug (an antibiotic substance such as ampicillin, tetracycline, kanamycin). The medium may further contain an oleanane-type triterpenoid monoglucuronide serving as a sugar acceptor substrate of the polypeptide described in the first aspect, preferably β-amyrin monoglucuronide, 11-oxo-β-amyrin monoglucuronide, 30-hydroxy-11-oxo-β-amyrin monoglucuronide, 30-hydroxy-β-amyrin monoglucuronide, 11-oxo-glycyrrhetinic acid monoglucuronide or glycyrrhetinic acid monoglucuronide and/or a sugar donor substrate, i.e., glucuronic acid.

The culture conditions are not particularly limited as long as they are appropriate conditions for expressing a polynucleotide. A culture is performed usually at a temperature of 10 to 45° C., 15 to 40° C. or 18 to 37° C., if necessary, while aerating, under irradiation, and/or with stirring for several hours to several hundreds of hours. As to a specific manner for this, see, for example, Green & Sambrook, Molecular Cloning, 2012, Fourth Ed., Cold Spring Harbor Laboratory Press.

To recover the polypeptide described in the first aspect from a culture (including culture supernatant or cultured transformant), the polypeptide accumulated in the culture is extracted by a known method and purified, as needed. A desired polypeptide can be obtained, for example, by a solvent extraction method, a salting method, a solvent precipitation method, a dialysis method, an ultrafiltration method, a gel electrophoresis method, a gel filtration chromatography, ion exchange chromatography, reversed phase chromatography and affinity chromatography, singly or in appropriate combination. As to a specific manner for this, see the method of Hayashi et al. (Hayashi et al., 1996, Phytochemistry, 42: 665-666) and the method of Noguchi et al. (Noguchi et al., 2007, J. Biol. Chem., 282: 23581-23590) mentioned above.

According to the method for producing the polynucleotide of the present invention, glucuronosyltransferase 2 and an active fragment thereof can be stably obtained in a large amount by using the host as a biological production system.

6. Method for Producing Glycyrrhetinic Acid Monoglucuronide

A sixth aspect of the present invention relates to a method for producing glycyrrhetinic acid monoglucuronide.

Glycyrrhetinic acid monoglucuronide is the same sweet substance as glycyrrhizin and highly valuable in the industrial field. However, since it is present in an extremely small amount in the nature, it is difficult to obtain glycyrrhetinic acid monoglucuronide in a large amount. However, as is clearly described in the specification, glycyrrhizin can be produced from glycyrrhetinic acid monoglucuronide in an individual or cell capable of biologically synthesizing glycyrrhizin from β-amyrin, by glucuronosyltransferase 2 described in the first aspect. In an individual or cell having the biosynthetic system, glycyrrhizin is accumulated in a cell as a chemically stable final product. However, if the activity of glucuronosyltransferase 2 is suppressed in the biosynthetic system, conversion of an oleanane-type triterpenoid monoglucuronide into an oleanane-type triterpenoid diglucuronide is suppressed. As a result, glycyrrhetinic acid monoglucuronide (oleanane-type triterpenoid monoglucuronide), which is a precursor of glycyrrhizin (oleanane-type triterpenoid diglucuronide), is accumulated as a final product in the cell. The present invention is directed to a method for producing glycyrrhetinic acid monoglucuronide based on such a principle.

The production method of the present invention includes a suppression step. The "suppression step" of the present aspect is the step of suppressing the activity of the polypeptide described in the first aspect in an individual or cell capable of biologically synthesizing glycyrrhizin from β-amyrin.

To the polypeptide described in the first aspect according to the present aspect, mainly glucuronosyltransferase 2 corresponds. Specifically, glucuronosyltransferase 2 containing an amino acid sequence represented by SEQ ID NO: 3; or glucuronosyltransferase 2 containing an amino acid sequence (GuUGT73.8) represented by SEQ ID NO: 4, an amino acid sequence derived from the amino acid sequence represented by SEQ ID NO: 4 by deletion, replacement or addition of one or several, or a plurality of amino acids, or an amino acid sequence having 80% or more identity with the amino acid sequence represented by SEQ ID NO: 4 corresponds thereto.

The "individual" in this step may be any one of a plant, an animal, a bacterium, a yeast and a fungus, as long as it can biologically synthesize glycyrrhizin from β-amyrin; however, preferably a plant, more preferably a Fabaceae plant, further preferably a Glycyrrhiza plant, a Medicago plant or a Glycine plant. More specifically, G. uralensis, M. truncatula or a Glycine max is mentioned. In the individual in this step, the gene encoding an enzyme contributing to a biosynthetic system from β-amyrin to glycyrrhizin may not be an endogenous gene of the individual. For example, the individual may be a transformant and a part of a gene encoding the enzyme in its biosynthetic system may be an exogenic gene. For example, a transformant prepared by introducing a foreign gene, i.e., CYP88D6 gene, into an individual, which does not have a gene encoding an enzyme having an activity of oxidizing carbon at the 11-position of an oleanane-type triterpenoid, can be used. Furthermore, as the "cell" in this step, a cell derived from the individual as mentioned above (including a part of an individual such as a tissue or an organ) is mentioned.

In this step, as a method for suppressing the activity of glucuronosyltransferase 2, for example, a method of suppressing expression of a gene encoding glucuronosyltransferase 2 or a method of directly suppressing the activity of the glucuronosyltransferase 2 by use of an activity inhibitor for glucuronosyltransferase 2, is mentioned. Suppression by these methods may be based on spontaneous mutation, or artificial treatment or mutation. Now, a method of suppressing expression of a gene and a method of using an activity inhibitor will be more specifically described.

(1) Method of Suppressing Expression of a Gene

The method of suppressing expression of a gene is a method of suppressing the expression of a target enzyme, glucuronosyltransferase 2, itself, thereby reducing an absolute amount of target enzyme in a cell, i.e., reducing a specific activity to the substrate. Suppression of gene expression may be not only complete suppression but also partial suppression. Such a method of suppressing gene expression is roughly divided into a transcription suppression method and post-transcription-pre-translation suppression method.

(i) Transcription Suppression Method

The transcription suppression method is a method of suppressing a gene encoding glucuronosyltransferase 2 (hereinafter referred to as a glucuronosyltransferase 2 gene) in an expression step in an individual or cell as mentioned above. The transcription suppression method for a gene is not particularly limited; however, for example, a molecular genetic method of artificially controlling gene expression, a method of controlling a transcription mechanism of the glucuronosyltransferase 2 gene, or a method of using a mutant of the gene, is mentioned.

As the molecular genetic method based on artificial control, for example, a method of exerting a desired function by modifying the promoter region of a glucuronosyltransferase 2 gene or by introducing a mutated glucuronosyltransferase 2 gene having addition, deletion (including gene destruction) and/or replacement of one or more nucleotides, into an individual or cell, is known. A mutation as mentioned above can be introduced to e.g., the glucuronosyltransferase 2 gene or a promoter region thereof in an individual or cell by a known method or an equivalent method thereto. For example, a method of introducing a mutation into a glucuronosyltransferase 2 gene, which is cloned by using e.g., a commercially available gene mutation introduction kit (e.g., Mutant-K (TaKaRa), Mutant-G (TaKaRa)) using a site-specific mutagenesis method or LA PCR in vitro Mutagenesis series kit (TaKaRa), and thereafter replacing with an endogenous wild type glucuronosyltransferase 2 gene by homologous recombination, is mentioned. As to a specific manner for this, for example, see the method described in Green & Sambrook, Molecular Cloning, 2012, Fourth Ed., Cold Spring Harbor Laboratory Press.

As the method of controlling the transcription mechanism of the glucuronosyltransferase 2 gene, for example, a method of suppressing a transcriptional factor, which specifically controls expression of the glucuronosyltransferase 2 gene, is mentioned. Specifically, e.g., a low molecular compound, an aptamer or an antibody, which inhibits the function or activity of a transcriptional factor, may be used.

As a method of using a mutant, a method of treating an individual or cell with a mutagenesis agent such as EMS or MNNG or with UV irradiation and thereafter separating a mutant having a defective activity of glucuronosyltransferase 2 by selecting, is mentioned. As to a specific manner for this, for example, see the method described in Green & Sambrook, Molecular Cloning, 2012, Fourth Ed., Cold Spring Harbor Laboratory Press.

The mutant having a mutation of the glucuronosyltransferase 2 gene can be used for elucidation of the biosynthetic system of glycyrrhizin.

(ii) Post-Transcription-Pre-Translation Suppression Method

The post-transcription-pre-translation suppression method is a method of suppressing mRNA, a transcriptional product of a glucuronosyltransferase 2 gene, in an individual or cell as mentioned above.

As a specific example of the post-transcription-pre-translation suppression method, a method of using an RNA interference agent, an aptamer, anti-sense DNA, a ribozyme (including deoxyribozyme) or U1 adaptor, is mentioned. The RNA interference agent refers to a substance capable of inducing RNA interference (RNAi) in vivo and degrading a transcriptional product of a target gene, thereby suppressing (silencing) expression of the gene. For example, siRNA (small interfering RNA), shRNA (short hairpin RNA) or miRNA (micro RNA) (including pri-miRNA and pre-miRNA) corresponds thereto. These methods are convenient since they have relatively high specificity to a transcriptional product of a target gene and a process for treatment is easy.

The RNA interference agent, aptamer, anti-sense DNA, ribozyme and U1 adaptor are all known. As to the RNA interference agent, see, for example, the method described in Bass B. L., 2000, Cell, 101, 235-238; Sharp P. A., 2001, Genes Dev., 15, 485-490; Zamore P. D., 2002, Science, 296, 1265-1269; Dernburg, A. F. & Karpen, G. H., 2002, Cell, 111, 159-162. As to the nucleic acid aptamer, see, for example, the method described in Sumedha D. Jayasena, 1999, Clin. Chem. 45: 1628-1650. As to the anti-sense DNA and ribozyme, see, for example, the method described in Green & Sambrook, Molecular Cloning, 2012, Fourth Ed., Cold Spring Harbor Laboratory Press. As to the U1 adaptor, see the method described in Goraczniak R., et al., 2009, Nat Biotechnol., Vol 27, p257-263.

(2) Method Using Activity Inhibitor

A method using an activity inhibitor is a method of directly or indirectly inhibiting the activity of a target enzyme, i.e., glucuronosyltransferase 2, by treating an individual or cell with a substance inhibiting the enzyme. Suppression of glucuronosyltransferase 2 may be not only complete suppression but also partial suppression.

As the activity inhibitor, a substance binding to a target glucuronosyltransferase 2 to directly suppress its activity, a substance degrading glucuronosyltransferase 2, or a substance binding to a substrate, i.e., an oleanane-type triterpenoid monoglucuronide competitively with glucuronosyltransferase 2 to indirectly suppress its activity, is mentioned.

As the substance binding to glucuronosyltransferase 2 to suppress the activity thereof, for example, an antibody against glucuronosyltransferase 2 or a fragment thereof (which serves as an antigen), an aptamer or a low-molecular compound, is mentioned. The antibody or aptamer can be prepared by a customary method in the art.

After the suppression step, glycyrrhetinic acid monoglucuronide may be extracted and recovered from an individual or cell by use of a conventional method of extracting and recovering glycyrrhizin, which is known in the art. As to the conventional method, see, for example, the method of Hayashi et al. (Hayashi et al., 2003, Biol. Pharm. Bull., 26: 867-871). According to the production method of the present invention, glycyrrhetinic acid monoglucuronide can be stably obtained as a final product at low cost and in a relatively large amount.

7. Method for Selecting Plant

A seventh aspect of the present invention relates to a method for selecting a plant by use of the polynucleotide described in the second aspect. The method is a method of detecting the presence or absence or expression of the polynucleotide described in the second aspect in a target plant, thereby selecting the plant having the polynucleotide described in the second aspect. The method includes detecting or quantifying the polynucleotide by subjecting a sample containing a nucleic acid prepared from a target plant to a nucleic acid amplification or nucleic acid hybridization using the polynucleotide or a fragment thereof.

In the present invention, the "target plant" refers to a plant to be subjected to the selecting method. The part of a plant body to be used is not particularly limited; however, a part where the polynucleotide described in the second aspect may be possibly expressed in a high level, for example, root or stolon, is preferable.

The sample containing a nucleic acid as mentioned above can be prepared from a target plant by a method known in the art, for example, a phenol extraction method, a phenol/chloroform extraction method or a CTAB method.

The "nucleic acid amplification" refers to a method of amplifying a specific nucleic acid region by a nucleic acid polymerase, for example, a PCR (polymerase chain reaction) method, a RT-PCR (reverse transcription polymerase chain reaction) method, an ICAN (Isothermal and Chimeric Primer-initiated Amplification of Nucleic Acids) method or a modified method thereof (e.g., real time PCR method). Preferably, a PCR method is used. This is because the PCR method is most widely used in the art throughout the world and many reagents, kits and reaction apparatuses and others are sufficiently provided and various modification methods are known.

The "nucleic acid hybridization method" is a method of detecting or quantifying a desired polynucleotide or a fragment thereof by using a nucleic acid fragment having a nucleotide sequence complementary to the nucleotide sequence of the desired polynucleotide or a fragment thereof, more specifically, by use of base pairing between the polynucleotide or a fragment thereof and the nucleic acid fragment. As the nucleic acid hybridization method, for example, a DNA-DNA hybridization method, a DNA-RNA hybridization method or an RNA-RNA hybridization method, is mentioned. As to these specific manners, see, for example, Northern hybridization (see, Molecular biology experiment protocol I (1997), translated by Nishino and Sano, Maruzen Co., Ltd.), DNA microarray method (see, DNA microarray and modern PCR method (2000), supervised by Muramatsu and Nawa, Shujunsha Co., Ltd.).

The primer or probe to be used in the nucleic acid amplification or nucleic acid hybridization may be designed based on any one of the nucleotide sequences described in the second aspect, preferably a nucleotide sequence represented by SEQ ID NO: 5 or the nucleotide sequence of a mutant or an orthologue gene thereof. The nucleic acids constituting the primer and/or probe of the present invention, which are usually DNA or RNA, may include, if necessary, a chemically modified nucleic acid and pseudo nucleic acid such as PNA (Peptide Nucleic Acid), LNA (Locked Nucleic Acid; registered trademark), methyl phosphonate type DNA, phosphorothioate type DNA or 2'-O-methyl type RNA. Alternatively, the primer and/or probe of the invention may be constituted of a combination thereof. Furthermore, the primer and the probe can be modified or labeled with a fluorescent dye (for example, fluorescamine or a derivative thereof, rhodamine or a derivative thereof, FITC, cy3, cy5, FAM, HEX, VIC), a quencher agent (TAMRA, DABCYL, BHQ-1, BHQ-2 or BHQ-3), a modifying substance such as biotin or (strepto) avidin, or magnetic beads, or an isotope (for example, $^{32}$P, $^{33}$P, $^{35}$S). The site of the primer or the probe to be modified or labeled with such a modifying substance may be appropriately determined in consideration with the properties of the modifying substance or the purpose of use. In general, 5' or 3' terminal is often modified. A single primer and probe molecule may be modified with one or more modifying substances.

The size of the primer and the probe to be used in the present invention is not particularly limited. In the case of the primer, usually a 15 to 50 nucleotide length and preferably a 17 to 30 nucleotide length is employed. In the case of the probe, more specifically, in the case of the probe to be used in Southern or Northern hybridization, at least from a 10 nucleotide length to the full length, preferably from a 15 nucleotide length to the full length, more preferably from a 30 nucleotide length to the full length and further preferably from a 50 nucleotide length to the full length, is employed. In the case of the probe to be used in DNA microarray, a 10 to 50 nucleotide length, preferably a 15 to 30 nucleotide length, more preferably a 20 to 25 nucleotide length is employed. However, the size of the probe is not limited to these. Generally, the longer the probe, the higher the hybridization efficiency and the higher the sensitivity. In contrast, the shorter the probe, the lower the sensitivity and the higher the specificity. A probe on a solid phase is prepared by spotting a solution of 0.1 μg to 0.5 μg. Specific examples of the primer and probe to be used include a set of primers for *G. uralensis*, SEQ ID NOs: 1 and 2 and a set of primers for *L. japonicus*, SEQ ID NOs: 6 and 7.

Conditions of the nucleic acid amplification vary depending upon e.g., length and amount of nucleotides of the nucleic acid fragment to be amplified and the length of nucleotides and Tm value of the primer to be used, and are thus appropriately determined depending upon these conditions. For example, in the case of a PCR method, a single cycle, which consists of a reaction at 94 to 95° C. for 5 seconds to 5 minutes, an annealing reaction at 50 to 70° C. for 10 seconds to 1 minute and an extension reaction at 68 to 72° C. for 30 seconds to 3 minutes, is repeated approximately 15 to 40 times and finally an extension reaction may be performed at 68 to 72° C. for 30 seconds to 10 minutes.

A nucleic acid amplification product can be detected by using, for example, agarose electrophoresis, polyacrylamide gel electrophoresis or dot hybridization. These nucleic acid amplification products can be quantified by using a chemiluminescence-imaging analyzer (for example, ATTO Corporation: Light Capture Series) or an imaging analyzer (for example, FUJIFILM: BAS Series).

An example of a method for quantifying an expression level of the polynucleotide described in the second aspect by a PCR method includes an RT-PCR method using an internal standard substance (see, forefront of PCR Method (1996), edited by Sekiya and Fujinaga, Kyoritsu Shuppan Co., Ltd). As the internal standard to be used, a housekeeping gene (for example, GAPDH, β-actin) is generally used. In this method, the relative amount of target mRNA to the internal standard sample can be obtained. During the PCR regarding a single sample, a reaction solution is sampled at the intervals of several cycles and then the amount of PCR product is quantified and plotted on a graph. The exponential amplification phase on the graph thus obtained is subjected to regression analysis to obtain an y-intercept. In this manner, an initial amount of template can be calculated (Biological Experiment Illustrated 3, "actually amplified by PCR)" (1998), written by Hiroki Nakayama, Shujunsha Co., Ltd.)

The expression level of the polynucleotide described in the second aspect can be quantified by a real-time quantitative PCR method. When a PCR is carried out in a reaction system in which a PCR product is specifically fluorescently labeled by using a thermal cycler equipped with an apparatus for detecting fluorescence intensity, the level of a product during the reaction can be monitored in real time without sampling and the results can be checked by regression analysis by a computer. Examples of a method for labeling a PCR product include a method using a probe fluorescently labeled (for example, a TaqMan (registered trademark) PCR method) and a method using a reagent specifically binding to a double-stranded DNA. The TaqMan (registered trademark) PCR method uses a probe having the 5'-terminal modified with a quencher substance and the 3'-terminal modified with a fluorescent dye. The quencher substance at the 5'-terminal suppresses the fluorescent dye at the 3'-terminal, under normal conditions; however, once PCR is conducted, a probe is degraded by a 5'→3' exonuclease activity of a Taq polymerase and then the suppression by the quencher substance is removed and florescence is produced. The amount of fluorescence reflects an amount of PCR product. Since the number of cycles (CT) when a PCR product reaches a detection limit and an initial amount of template are inversely correlated, the initial amount of template is quantified by measuring CT in a real-time measurement method. If a calibration curve is prepared by measuring CT at several known amounts of template, the absolute value of initial amount of template of an unknown sample can be calculated. Examples of reverse transcriptase that can be used in an RT-PCR include M-MLV RTase and ExScript RTase (TaKaRa) and Super Script II RT (GIBCO-BRL).

When nucleic acid hybridization is carried out, not only the above-mentioned probe but also a nucleic acid in a sample may be modified/labeled. For modification/labeling, an isotope (e.g., $^{32}$P, $^{33}$P, $^{35}$S) or a fluorescent substance (fluorescamine and a derivative thereof, rhodamine and a derivative thereof, FITC, Cy3 or Cy5) can be used. Modification/labeling may be appropriately carried out depending upon the purpose and is not particularly limited.

Hybridization is preferably carried out under stringent conditions as mentioned above in order to eliminate non-specific hybridization with undesired nucleic acids.

A Northern hybridization method is generally used for detecting and quantifying an RNA sequence. An RNA sample, which is obtained from a plant by a known method, is separated by agarose gel electrophoresis. The RNA fractions thus separated are transferred to a nylon or nitrocellulose membrane. Then, hybridization is performed by using cDNA or a fragment thereof labeled with the polynucleotide described in the second aspect as a probe. In this manner, a desired polynucleotide can be detected or quantified.

In a DNA microarray method, cDNA, or a sense strand or an antisense strand thereof encoding the polynucleotide of the present invention or a fragment thereof is immobilized as a probe onto an array of glass or filter. A reverse transcription reaction is performed using RNA obtained by a known method to synthesize a cDNA molecule while introducing e.g., Cy3-dUTP, Cy5-dUTP to obtain a labeled cDNA molecule. Then, the probe immobilized onto the array is hybridized with the labeled cDNA molecule to detect and quantify the polynucleotide of the invention. In this manner, a plant having a high content of glycyrrhizin can be selected and screened.

Note that as to the specific manner for the above-mentioned molecular biological techniques, see Green & Sambrook, Molecular Cloning, 2012, Fourth Ed., Cold Spring Harbor Laboratory Press.

EXAMPLES

The present invention will be described by way of examples below.

Example 1: Preparation of mRNA From *Glycyrrhiza* Plant and Construction of cDNA Library (1)

A stolon of 7-year-old *G. uralensis* cultivated in a field at the Research Center for Medicinal Plant Resources, Hokkaido Division (Nayoro city, Hokkaido) of the National Institute of Biomedical Innovation was harvested in June. Total RNA was prepared by using an RNA extraction reagent, RNAwiz™ (Ambion, Inc.) in accordance with the attached protocol. From the total RNA thus obtained, mRNA was prepared and then cDNA was synthesized by a vector-capping method (Kato, S. et al., DNA Res., 12, 53-62, 2005). Then, the cDNA fragments thus obtained were inserted into a plasmid vector pGCAPzf3 (Tsugane, T. et al., Plant Biotechnology., 22, 161-165, 2005) to construct a cDNA library.

Example 2: Preparation of mRNA From *Glycyrrhiza* Plant and Construction of cDNA Library (2)

A stolon of *G. uralensis,* which had been presumably cultivated in a field for four years or longer after settled planting at the Research Center for Medicinal Plant Resources, Tsukuba Division (Tsukuba city, Ibaraki) of the National Institute of Biomedical Innovation, was harvested in October. Total RNA was prepared by using an RNA extraction reagent, TRIzol (registered trademark) (life technologies) and a purification column RNeasy (registered trademark) (Quiagen) in accordance with the attached protocol. From the total RNA thus obtained, mRNA was prepared and then cDNA was synthesized by an oligo-capping method (Murayama, K. et al., Gene, 138, 171-174, 1994 and Suzuki, Y. et al., Gene, 200, 149-156). Then, the cDNA fragments thus obtained were inserted into a plasmid vector pCMVFL3 to construct a cDNA library.

Example 3: Sequence Analysis (1)

A strain of *E. coli,* DH12S (life technologies) or DH10B T1 phage-resistant (life technologies) was transformed with the cDNA library obtained in Example 1. Of the colonies obtained, approximately 30,000 single colonies were picked up and inoculated on 384 plates. DNA to be used as a template of a sequencing reaction in a colony PCR was amplified and purified by ethanol precipitation. Using the DNA purified as a template, a sequencing reaction was carried out from the 5' terminal side of each cDNA fragment with BigDye ver 3.1 (Applied Biosystems). After purified with ethanol precipitation, nucleotide sequence was analyzed by 3730×1 DNA Analyzer (Applied Biosystems).

Example 4: Sequence Analysis (2)

A strain of *E. coli,* DH5α, was transformed with the cDNA library obtained in Example 2. Of the colonies obtained, approximately 26,000 single colonies were picked up and inoculated on 384 plates. DNA to be used as a template of a sequencing reaction in a colony PCR was amplified and purified by ethanol precipitation. Using the DNA purified as a template, a sequencing reaction was carried out from the 5' terminal side of each cDNA fragment with BigDye ver 3.1 (Applied Biosystems). After purified with ethanol precipitation, the nucleotide sequence was analyzed by 3730×1 DNA Analyzer (Applied Biosystems).

Example 5: Clustering of EST (Expressed Sequence Tag)

Approximately 30,000 EST data obtained in Example 3 and approximately 26,000 EST data obtained in Example 4 were integrated into a single data set and clustering was carried out by using a PHRAP program. As a result, 10,372 unique contigs were obtained.

Figure 2:
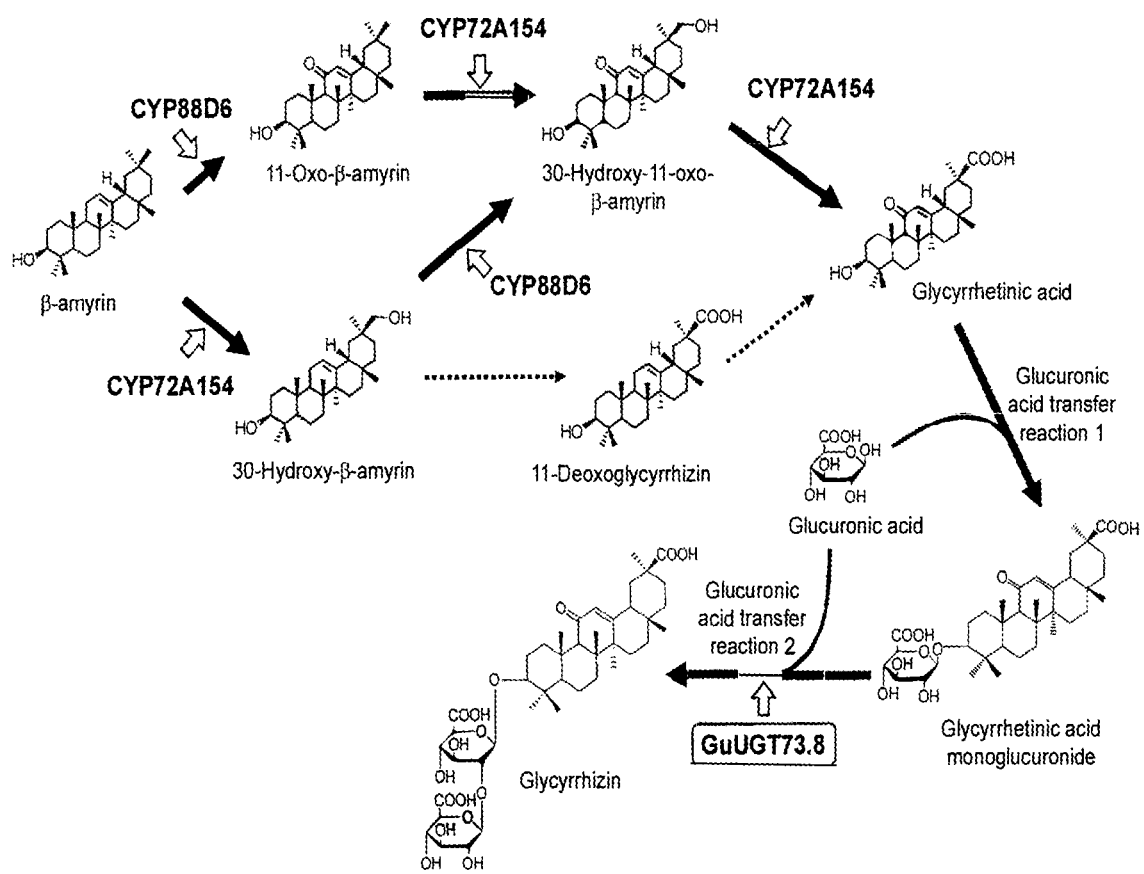
FIG. 2 shows an oleanane-type triterpenoid in a biosynthetic pathway from β-amyrin to glycyrrhizin and the steps catalyzed by known enzymes (CYP88D6, CYP72A154, GuUGT73.8) involved in conversion reactions. GuUGT73.8 corresponds to a glucuronosyltransferase 2 of the present invention.

Example 6: Extraction of Family 1 Glycosyltransferase Gene Through Homology Search A BLASTX® search (Altschul, S. F. et al., Nucleic Acids Res. 25, 3389-3402, 1997) was carried out for known proteins registered in the database of NCBI (National Center for Biotechnology Information) using 10,372 contig sequences obtained in Example 5 as queries. The present inventors predicted that family 1 glycosyltransferase gene was involved in glycyrrhizin biosynthetic pathway (FIG. 2) on and after glycyrrhetinic acid and contigs having a high homology with known family 1 glycosyltransferase registered in the database were selected. Plasmid DNA was prepared from a clone determined to have the longest 5' terminal region from a plurality of EST clones constituting the selected contigs and full-length nucleotide sequence of each of cloned cDNA fragments (31 fragments) was determined.

Example 7: Gene Expression Analysis (Selecting of Candidate Gene)

In order to select a molecular species which is highly possibly involved in biosynthesis of glycyrrhizin from group of 31 family 1 glycosyltransferase genes obtained in Example 6, which organ of the plant body expresses each family 1 glycosyltransferase molecular species was investigated by an RT-PCR method. Total RNA was prepared from four types of different plant tissues, in total, including an underground tissue (thickened root and stolon) where glycyrrhizin is highly accumulated and an aboveground tissue (leave and stem) where glycyrrhizin is not detected. Using 1 μg of the total RNA obtained, a first-strand cDNA was synthesized by use of a SMART RACE cDNA amplification kit (Clontech) in accordance with the attached protocol.

Subsequently, sense primers and antisense primers specifically annealing with each family 1 glycosyltransferase gene were designed and a cycle of PCR was repeated 25 to 30 times by use of Ex Taq™ DNA polymerase (TaKaRa) and four types of first-strand cDNA molecules (2 µL for each) as templates. The PCR fragments thus obtained were analyzed by agarose gel electrophoresis and family 1 glycosyltransferase molecular species highly expressed in root and stolon were selected.

Figure 3:
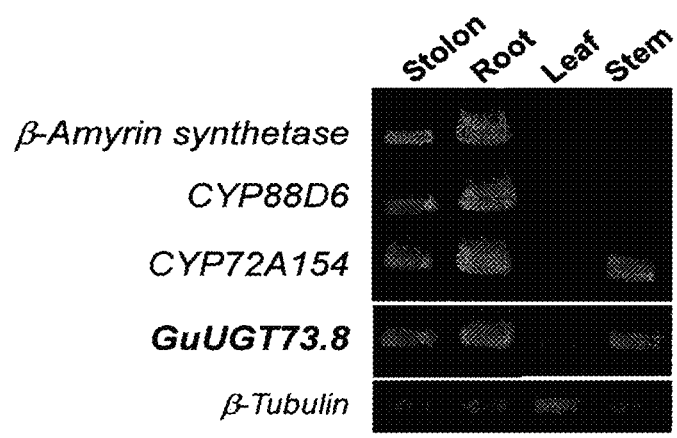
FIG. 3 shows analysis results of gene expression by an RT-PCR method.
Figure 4A:
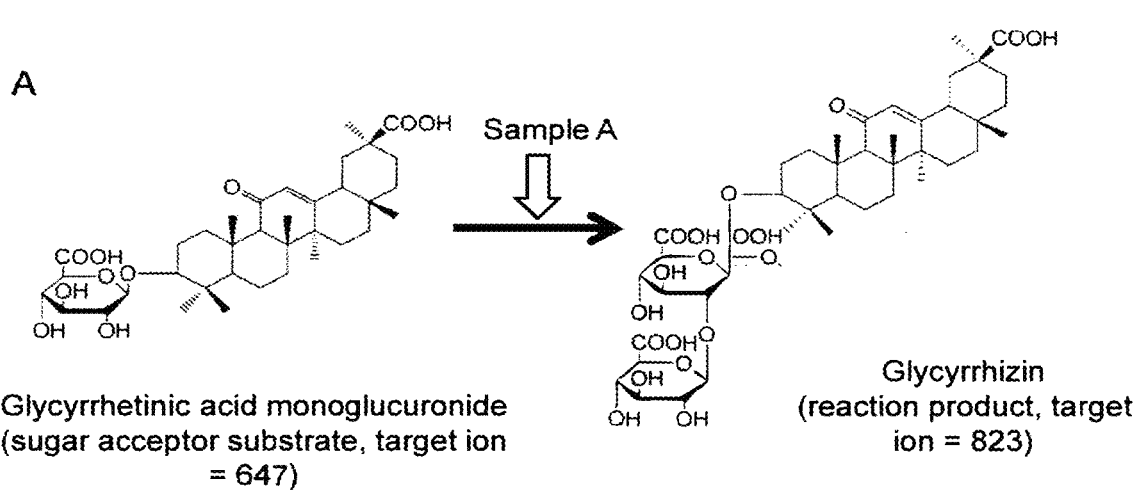
FIG. 4-A A. shows a conceptual diagram when sample A was used. B. shows detection results of glycyrrhetinic acid monoglucuronide before glycyrrhetinic acid monoglucuronide is converted to glycyrrhizin by the polypeptide (GuUGT73.8) of the present invention. The peak pointed by an open arrow shows glycyrrhetinic acid monoglucuronide. C. shows results of LC-MS analysis of a reaction solution, which was prepared by adding sample A, which is a protein extract obtained from a transformed yeast expressing GuUGT73.8, to a solution containing a sugar acceptor substrate, i.e., glycyrrhetinic acid monoglucuronide, and a sugar donor substrate, i.e., UDP-glucuronic acid, and which was subjected to in vitro enzyme assay. The peak pointed by a solid arrow shows glycyrrhizin.
Figure 4A:
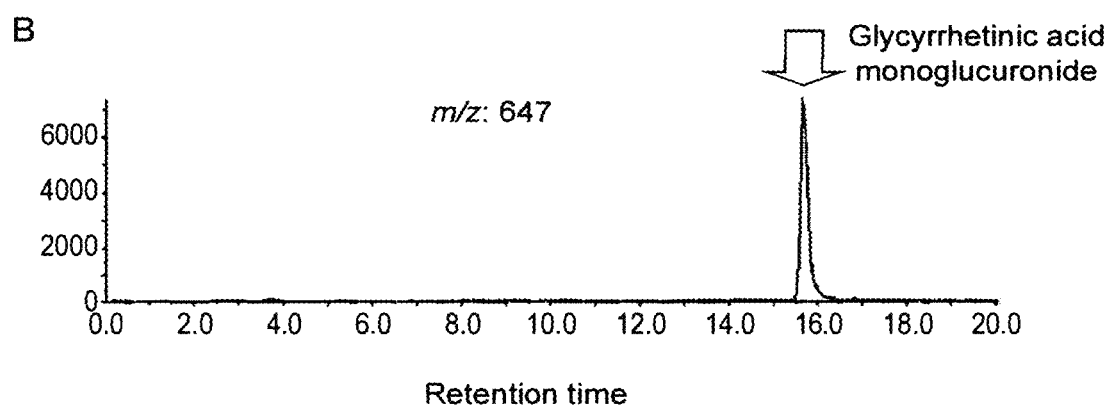
Figure 4A:
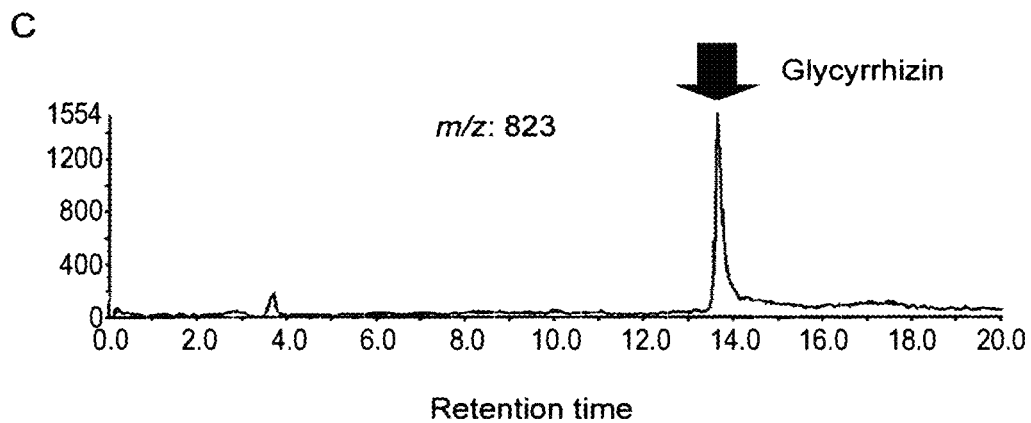
Figure 4B:
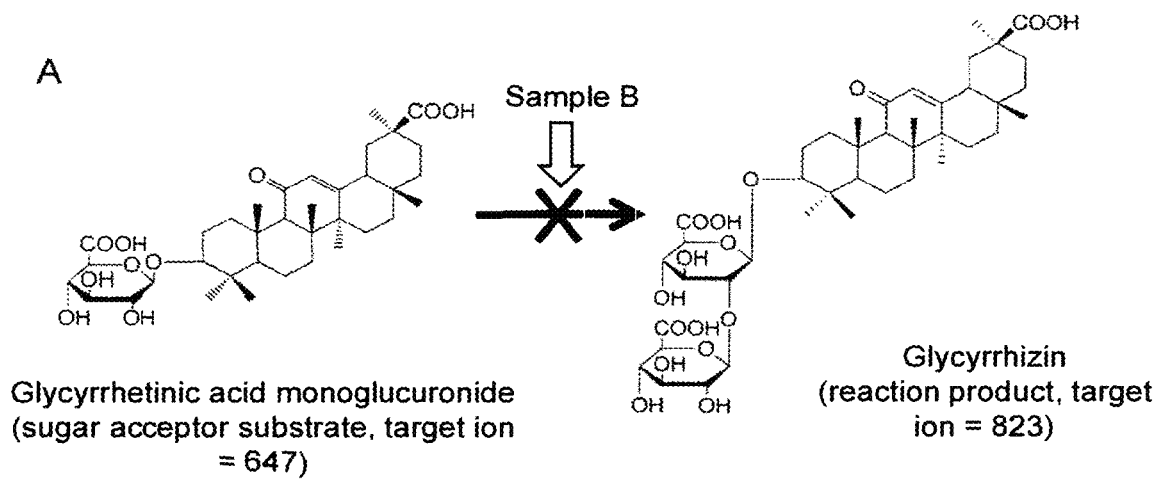
Figure 4B:
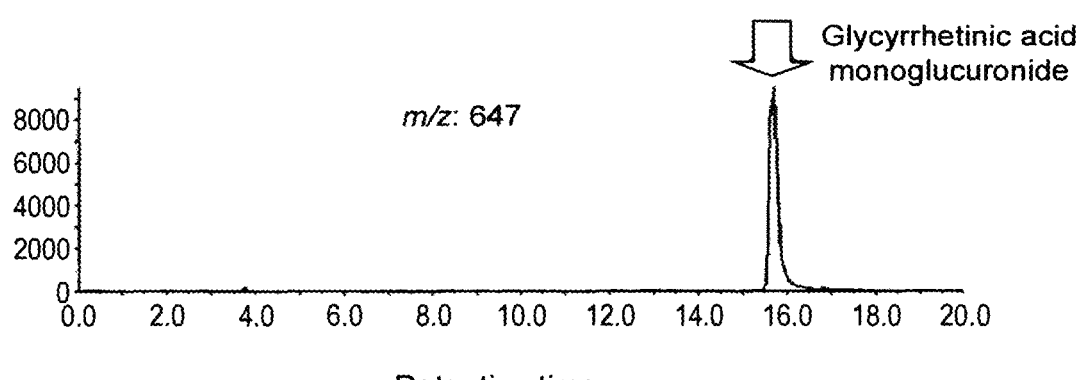
Figure 4B:
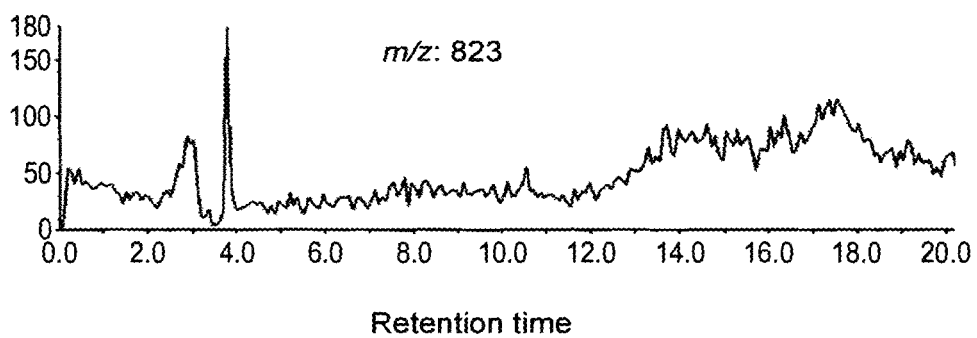

Part of the results is shown in FIG. 3. It is found that a β-amyrin synthase (bAS: β-amyrin synthase) gene (see FIG. 1) and CYP88D6 gene and CYP72A154 gene (see FIG. 2) involved in the biosynthetic system of glycyrrhizin are strongly expressed in stolon and root. The same expression pattern was confirmed also in GuUGT73.8 gene (shown in FIG. 3) of 31 candidate genes obtained in Example 6. Then, GuUGT73.8 gene was subjected to the experiments shown in following Examples.

Example 8: Cloning of GuUGT73.8 Gene

Full-length glucuronic acid transfer enzyme candidate GuUGT73.8 obtained by selecting in Example 7 was cloned.

The full-length coding region of the GuUGT73.8 gene was isolated. More specifically, the cycle of PCR was repeated 30 times by use of KOD-plus-DNA Polymerase (TOYOBO) at an annealing temperature of 56° C. and a reaction temperature of 68° C., using a first-strand cDNA prepared by using total RNA derived from thickened root and produced in Example 7 as a template and using oligo DNA molecules corresponding to the N terminal and C terminal of GuUGT73.8 polypeptide, respectively as a forward primer (SEQ ID NO: 1) and a reverse primer (SEQ ID NO: 2). Note that 4 nucleotides (cacc) are added to the 5' terminal of the forward primer represented by SEQ ID NO: 1. This is for use in cloning to pENTR™/D-TOPO (registered trademark) entry vector (life technologies). The DNA fragment amplified by PCR was cloned to pENTR™/D-TOPO (registered trademark) entry vector. The nucleotide sequences of the resultant three independent clones (pENTR™/D-TOPO-GuUGT73.8) were determined. As a result, the nucleotide sequence of the GuUGT73.8 gene obtained is represented by SEQ ID NO: 5. The amino acid sequence of GuUGT73.8, which is estimated from the nucleotide sequence, is represented by SEQ ID NO: 4.

Homology search was performed by BLAST®. As a result, it was found that GuUGT73.8 having the amino acid sequence represented by SEQ ID NO: 4 is a novel protein.

Example 9: Search for GuUGT73.8 Orthologue Gene Derived From *L. japonicus*

An orthologue gene, which is expected to have an analogous function to GuUGT73.8 gene in *L. japonicus* belonging to the same *Fabaceae* plant as *G. uralensis*, was searched.

Using BLAST® homology search function in genome information database of *L. japonicus*, two types of partial nucleotide sequences, LjSGA_046111 and LjSGA_014618, which may encode proteins having high amino acid identity with GuUGT73.8, were found. These sequences are partly overlapped. From this, it was estimated that they might respectively encode the N terminal region and C terminal region of the same polypeptide. The polypeptides estimated from LjSGA_046111 and LjSGA_014618 had an amino acid identity of 66% with that of GuUGT73.8.

Example 10: Isolation of *Lotus japonicus*-Derived GuUGT73.8 Homologous Gene

*L. japonicus* (MG20) was grown in a plant growth chamber (23° C., day-length: 16 hours). Total RNA was prepared from each of leaf and root of the plant on the 4th week after germination. Using the total RNA (1 µg) obtained, a first-strand cDNA was synthesized by use of SMART RACE cDNA amplification kit (Clontech) in accordance with the attached protocol. A cycle of PCR was repeated 35 times by use of KOD plus ver.2 polymerase (TOYOBO) at an annealing temperature of 56° C. and a reaction temperature of 68° C., using the first-strand cDNA (2 µL for each) as a template and oligo DNA molecules corresponding to the N terminal and C terminal of the polypeptide estimated from LjSGA_046111 and LjSGA_014618, respectively, as a forward primer (SEQ ID NO: 6) and a reverse primer (SEQ ID NO: 7). Note that 4 nucleotides (cacc) are artificially added to the 5' terminal of the primer represented by SEQ ID NO: A, for the reason that the nucleotides are required for cloning into pENTR™/D-TOPO (registered trademark) entry vector (life technologies). The DNA fragment, which was amplified from root-derived first-strand cDNA, was cloned to pENTR™/D-TOPO entry vector. The polynucleotide sequences of the resultant three independent clones were determined. As a result, the polynucleotide sequence thus obtained is represented by SEQ ID NO: 8. The polypeptide sequence estimated from the polynucleotide sequence is represented by SEQ ID NO: 9. The amino acid sequence represented by SEQ ID NO: 9 had an identity of 66.9% with the amino acid sequence represented by SEQ ID NO: 4.

Example 11: Construction of Yeast Expression Vector

A plasmid (entry clone) having the polynucleotide represented by SEQ ID NO: 5 produced in Example 8 and a destination vector pYES-DEST52 (life technologies) were mixed with each other and subjected to a nucleotide sequence specific recombination reaction (GATEWAY attL× attR reaction) using Gateway LR Clonase II Enzyme Mix (life technologies) to transfer the DNA fragment represented by SEQ ID NO: 5 to pYES-DEST52. In this manner, a yeast expression vector pDEST52-GuUGT73.8 for a gene represented by SEQ ID NO: 5 was obtained.

Example 12: Preparation of Transformed Yeast

To yeast INVSc1 strain (life technologies) (MATa his3D1 leu2 trp1-289 ura3-52 MATAlpha his3D1 leu2 trp1-289 ura3-52), pDEST52-GuUGT73.8 obtained in Example 11 was introduced. As a negative control, pYES2/CT (life technologies) corresponding to an empty vector was introduced into the INVSc1 strain. The yeast was transformed by use of Frozen-EZ Yeast Transformation II (Zymo Research) in accordance with the attached protocol.

Example 13: Expression of GuUGT73.8 in Transformed Yeast

Using 10 mL of Yeast nitrogen base (YNB) medium (-Ura) containing 2% raffinose, a transformed yeast having pDEST52-GuUGT73.8 or a negative control pYES2/CT was cultured while shaking at 30° C., 165 rpm for 25 hours. Thereafter, 1 mL of 20% galactose was added thereto and further cultured while shaking at 30° C. for 25 hours. The culture solution was centrifuged at 3,000 g, 4° C. for 10 minutes to obtain a yeast cell pellet. The yeast cell pellet thus obtained was suspended in 400 μL of extraction buffer (pH7.0, 50 mM Tris, 1 mM DTT, 14.4 mM β-mercaptoethanol, 20% Glycerol). To this, the same volume of glass beads (SIGMA) was then added. In order to fracture yeast cells, the suspension solution was vigorously stirred for 30 seconds by a vortex mixer, thereafter immediately transferred onto ice in order to prevent inactivation of enzyme activity by a temperature rise and allowed to stand still for one minute. This operation was repeated 15 times. The resultant solution was centrifuged at 10,000 g, 4° C. for 10 minutes and then the supernatant was recovered as a yeast protein extract. As a result, a protein extract (sample A) derived from a transformed yeast and expressing polypeptide (GuUGT73.8) represented by SEQ ID NO: 3 and a protein extract (sample B) derived from the transformed yeast with an empty vector and expressing no GuUGT73.8 were obtained. Protein concentration of each of Sample A and Sample B was measured by use of Bio-Rad Protein Assay (Bio-Rad).

Example 14: In Vitro Enzyme Assay Using Yeast Protein Extract

Each (200 μg) of Sample A and sample B (adjusted to a volume of 80 μL) obtained in Example 13, 10 μL of 1M tris-hydrochloric acid buffer (pH7.0), 5 μL of 400 mM MgCl$_2$, 0.2 μL of 14.4 mM β-mercaptoethanol, 4 μL of 30 mM glycyrrhetinic acid monoglucuronide (sugar acceptor substrate), 10 μL of 100 mM UDP-glucuronic acid (sugar donor substrate) and 91 μL of sterilized water were mixed and thereafter incubated for 24 hours while stirring at 30° C., 1,000 rpm to perform a sugar (glucuronic acid) transfer reaction. After the incubation, the obtained solutions were designated as reaction solution A and reaction solution B.

Example 15: Identification of Converted Product

Reaction solutions A and B obtained in Example 14 were extracted with 200 μL of 1-butanol. 1-Butanol extract (100 μL) and methanol (400 μL) were mixed and used as a sample for LC-MS analysis. LC-MS analysis was performed by an apparatus prepared by connecting an LC unit (1100 series, Agilent Technologies) and an MS unit (QSTAR PULSAR, Applied Biosystems). As a column, Senshu PA K 25 cm×2 mm i.d was used. Analysis was made while supplying solvents containing 0.1% acetic acid-acetonitrile: 0.1% acetic acid-water=20:80 (0 to 2 minutes), 20:80 to 95:5 (2 to 12 minutes) and 95:5 (12 to 20 minutes) at a flow rate of 0.2 mL/minute. The converted product was identified by comparing LC retention times and MS spectra of glycyrrhetinic acid monoglucuronide and glycyrrhizin prepared in Example 14 as standards.

Enzyme assay of sample A in Example 14 was performed. As a result, a peak (FIG. 4-A: open arrow) corresponding to glycyrrhetinic acid monoglucuronide (sugar acceptor substrate) was detected from reaction solution A. In addition, a peak (FIG. 4-A, solid arrow) conceivably derived from glycyrrhetinic acid monoglucuronide to which a single glucuronic acid molecule was added was detected. The retention time and mass spectrum of this peak satisfactorily coincide with those of glycyrrhizin.

In contrast, from reaction solution B obtained by enzyme assay of sample B (a negative control) in Example 14, a peak (FIG. 4-B: open arrow) corresponding to glycyrrhetinic acid monoglucuronide (sugar acceptor substrate) was detected similarly to FIG. 4-A. However, a peak corresponding to glycyrrhizin pointed by the solid arrow in FIG. 4-A was not detected.

From the aforementioned results, novel enzyme GuUGT73.8 obtained in Example 7 was identified as novel glucuronosyltransferase 2 having glucuronic acid transfer activity 2, which converts glycyrrhetinic acid monoglucuronide to glycyrrhizin, by further transferring glucuronic acid to the hydroxy group at the 2-position of glycyrrhetinic acid monoglucuronide.

All publications, patents and patent applications cited in the specification as references are incorporated in their entirety herein.

---

The invention claimed is:

1. An isolated cDNA encoding a recombinant polypeptide having a sequence selected from the group consisting of
   (a) the amino acid sequence represented by SEQ ID NO:4, and
   (b) an amino acid sequence comprising SEQ ID NO:3 and that is at least 90% identical to SEQ ID NO:4,
   wherein the recombinant polypeptide has an activity to transfer glucuronic acid to the hydroxy group at the 2-position of glucuronic acid in an oleanane-type triterpenoid monoglucuronide.

2. The isolated cDNA according to claim 1, wherein the oleanane-type triterpenoid monoglucuronide is selected from the group consisting of β-amyrin monoglucuronide, 11-oxo-β-amyrin monoglucuronide, 30-hydroxy-11-oxo-β-amyrin monoglucuronide, 30-hydroxy-β-amyrin monoglucuronide, 11-oxoglycyrrhetinic acid monoglucuronide and glycyrrhetinic acid monoglucuronide.

3. The isolated cDNA according to claim 1, wherein the amino acid sequence is obtained from a *Glycyrrhiza* plant or a *Medicago* plant.

4. The isolated cDNA according to claim 3, wherein the *Glycyrrhiza* plant is *G. uralensis*.

5. The isolated cDNA according to claim 1, comprising the nucleotide sequence represented by SEQ ID NO: 5.

6. A recombinant vector comprising the isolated cDNA according to claim 1.

7. The recombinant vector according to claim 6, which is an expression vector for yeast.

8. The recombinant vector according to claim 6, which is an over-expression vector or a constitutive expression vector.

9. A transformant comprising the recombinant vector according to claim 6 or a progeny thereof which comprises the recombinant vector.

10. The transformant or a progeny thereof according to claim 9, which is a yeast.

11. A method for producing a polypeptide having an activity to transfer glucuronic acid to the hydroxy group at the 2-position of glucuronic acid in an oleanane-type triterpenoid monoglucuronide, comprising culturing the transformant or progeny thereof according to claim 9 and extracting the polypeptide encoded by the polynucleotide from the culture.

12. The isolated cDNA according to claim 1, wherein the recombinant polypeptide has the amino acid sequence represented by SEQ ID NO:4.

13. The isolated cDNA according to claim 1, wherein the recombinant polypeptide has the amino acid sequence comprising SEQ ID NO:3 and that is at least 90% identical to SEQ ID NO:4.

14. The isolated cDNA according to claim 1, wherein the recombinant polypeptide has the amino acid sequence comprising SEQ ID NO:3 and that is at least 95% identical to SEQ ID NO:4.

15. The isolated cDNA according to claim 1, wherein the recombinant polypeptide has the amino acid sequence comprising SEQ ID NO:3 and that is at least 97% identical to SEQ ID NO:4.

* * * * *